US012716787B2

(12) United States Patent
Sayde et al.

(10) Patent No.: US 12,716,787 B2
(45) Date of Patent: Aug. 25, 2026

(54) HIGH-RESOLUTION SEDIMENT DYNAMICS, WATER DEPTH, AND WATER VELOCITY SENSING SYSTEM

(71) Applicant: North Carolina State University, Raleigh, NC (US)

(72) Inventors: Chadi Sayde, Raleigh, NC (US); Celso Castro-Bolinaga, Raleigh, NC (US); Rebecca Hillman, Raleigh, NC (US); Mahmoud Shehata, Raleigh, NC (US)

(73) Assignee: NORTH CAROLINA STATE UNIVERSITY, Raleigh, NC (US)

(*) Notice: Subject to any disclaimer, the term of this patent is extended or adjusted under 35 U.S.C. 154(b) by 262 days.

(21) Appl. No.: 18/381,045

(22) Filed: Oct. 17, 2023

(65) Prior Publication Data

US 2024/0125656 A1 Apr. 18, 2024

Related U.S. Application Data

(60) Provisional application No. 63/416,705, filed on Oct. 17, 2022.

(51) Int. Cl.

*G01K 11/3206* (2021.01)
*E02D 5/34* (2006.01)
(Continued)

(52) U.S. Cl.

CPC ............ *G01K 11/3206* (2013.01); *E02D 5/34* (2013.01); *G01K 1/026* (2013.01); *G01K 1/045* (2013.01);
(Continued)

(58) Field of Classification Search

CPC .. G01K 11/3206; G01K 11/026; G01K 1/045; G01K 1/065; G01K 1/16;
(Continued)

(56) References Cited

U.S. PATENT DOCUMENTS

| | | | | |
|---|---|---|---|---|
| 6,783,273 B1 * | 8/2004 | Mullins | ................ | G01N 33/383 374/53 |
| 2015/0276702 A1 * | 10/2015 | England | ................ | G01K 13/10 374/4 |
| 2016/0298960 A1 * | 10/2016 | Hill | ................ | G01B 21/18 |

FOREIGN PATENT DOCUMENTS

| | | | | |
|---|---|---|---|---|
| EP | 0825459 A2 * | 2/1998 | ............. | G01V 9/005 |
| WO | WO-2014056541 A1 * | 4/2014 | ........... | G01B 21/085 |

OTHER PUBLICATIONS

Jeff Dagel, Dave Schoenwald; "Electricity Transmission System Research and Development: Automatic Control Systems" from the Office of Electricty, U.S. Department of Energy. (Year: 2021).*

* cited by examiner

*Primary Examiner* — Randy W Gibson
(74) *Attorney, Agent, or Firm* — Thomas | Horstemeyer, LLP

(57) ABSTRACT

Various examples are provided related to high-resolution sediment sensing including, e.g., water depth and/or water velocity sensing. In one example, a sediment dynamics monitoring system for scour, erosion or deposition detection includes a fiber-optic distributed temperature sensing (FO-DTS) sediment dynamics monitoring device including a support structure; a FO cable providing continuous sensing along a length of the support structure; and a heating element collocated along the FO cable; a power controller configured to control heating of the heating element; and a DTS system that can measure a temperature profile along a length of the FO cable. An anomaly in the measured temperature profile indicates an interface surrounding the FO-DTS sediment dynamics monitoring device. interface can be a sediment-water interface or a water-air interface.

20 Claims, 20 Drawing Sheets

(51) Int. Cl.

| | |
|---|---|
| ***G01K 1/02*** | (2021.01) |
| ***G01K 1/04*** | (2006.01) |
| ***G01K 1/06*** | (2006.01) |
| ***G01K 1/16*** | (2006.01) |
| ***G01N 25/72*** | (2006.01) |
| *E02D 5/40* | (2006.01) |
| *G01B 21/08* | (2006.01) |
| *G01N 33/38* | (2006.01) |

(52) U.S. Cl.
CPC ............... *G01K 1/065* (2013.01); *G01K 1/16* (2013.01); *E02D 5/40* (2013.01); *G01B 21/085* (2013.01); *G01K 2213/00* (2013.01); *G01K 2215/00* (2013.01); *G01N 25/72* (2013.01); *G01N 33/383* (2013.01)

(58) Field of Classification Search
CPC ........... G01K 2213/00; G01K 2215/00; G01K 13/026; G01K 11/32; G01B 21/085; G01N 25/72; G01N 33/383; E02D 5/34; E02D 5/40
See application file for complete search history.

DTS
115
103
(+)
10 AWG
0.30 m
(-)
106
0.05 m
Power Controller
112

1) Outer sheath (Ø= 3.8 mm, layer thickness = 0.2mm)
2) Stainless steel wires
3) Stainless steel protective tube
4) Multimode optical fiber with acrylic coating (Ø= 50 µm)
103
109
1
2
3
4

HIGH-RESOLUTION SEDIMENT DYNAMICS, WATER DEPTH, AND WATER VELOCITY SENSING SYSTEM

CROSS REFERENCE TO RELATED APPLICATIONS

This application claims priority to, and the benefit of, U.S. provisional application entitled "High-Resolution Scour, Water Depth, and Water Velocity Sensing System" having Ser. No. 63/416,705, filed Oct. 17, 2022, which is hereby incorporated by reference in its entirety.

BACKGROUND

Scour refers to the removal of sediment around riverine infrastructure due to the erosive action of flowing water. On the other hand, sediment deposition or sedimentation occurs when the flow velocity decreases allowing the suspended sediment to settle down. Changes in the hydraulic conditions of a waterway can trigger sediment scouring, sediment deposition, and/or bank erosion dynamics that can lead to significant changes in the waterway geomorphology. Additionally, local scouring around water structures can lead to their failure. For instance, scour is the leading cause of bridge failure in the United States. Scour around bridge foundations (e.g., piers and abutments) remains a major technical, societal, and economical challenge in the United States. Scour is responsible for nearly 60% of bridge failures, resulting in an average estimated annual cost of $30 million.

Moreover, numerical methods that are most commonly used to predict scour around bridge piers generally overpredict the amounts of scour depth, leading to safer but less cost-effective designs due to the over specification of expensive foundations and countermeasures. With more than 23,000 scour-critical bridges in the United States, accurate simultaneous measurements of scour depths and driving water flow conditions (e.g., depth and velocity) are of paramount importance, especially when considering the effects that climate change is having—and will continue to have—on the timing and intensity of storms. To date, no practical technology exists that allows simultaneous assessment of the hydraulic conditions, such as water depth and water velocity profile, around water structures while simultaneously providing information on sediment dynamics including transport rates and active scour formation.

SUMMARY

Aspects of the present disclosure are related to high-resolution sediment dynamics sensing that is capable of measuring other parameters including, e.g., air, water, and sediment temperatures, water depth, and/or water velocity. In one aspect, among others, a sediment dynamics monitoring system for scour, erosion and/or deposition detection comprises a fiber-optic distributed temperature sensing (FO-DTS) sediment dynamics monitoring device comprising: a support structure; a FO cable wound around the support structure, the FO cable providing continuous sensing along a length of the support structure; and a heating element collocated along the FO cable; a power controller configured to control heating of the heating element; and a distributed temperature sensing (DTS) system configured to measure a temperature profile along a length of the FO cable, wherein an anomaly in the measured temperature profile indicates an interface surrounding the FO-DTS sediment dynamics monitoring device.

In one or more aspects, the temperature profile can correspond to a heat pulse applied to the heating element for a defined period of time. The power controller can control application of power to the heating element over the defined period of time. The heating element can be incorporated in the FO cable. The heating element can comprise wires distributed about one or more optical fiber of the FO cable. The heating element can be wrapped adjacent to the FO cable. The heating element can be wrapped on the FO cable opposite the support structure. The FO-DTS sediment dynamics monitoring device can be positioned in sediment of a waterway and the interface is a sediment-water interface or an air-water interface. The DTS system can be configured to: detect a location of a minimum observed temperature along the FO-DTS sediment dynamics monitoring device; calculate a gradient of the measured temperature profile; and determine a location of a sediment-water interface, wherein the location of the sediment-water interface corresponds to a location of a minimum temperature gradient observed between an end of the FO-DTS sediment dynamics monitoring device located inside the sediment and the location of the minimum observed temperature. The DTS system can further be configured to: detect a location of a maximum observed temperature along the FO-DTS sediment dynamics monitoring device; and determine a location of an air-water interface in response to the location of the maximum observed temperature being above the location of the minimum observed temperature, wherein the location of the air-water interface that corresponds to a location of a maximum temperature gradient observed between the location of the minimum observed temperature and the location of the maximum observed temperature. The FO-DTS sediment dynamics monitoring device can be totally submerged underwater if the location of the maximum observed temperature is below the location of the minimum observed temperature.

In various aspects, the DTS system can be configured to identify a location of the interface along the length of the support structure based upon the temperature profile. The interface can be identified based upon a temperature gradient of the temperature profile. The DTS system is configured to: detect locations of a maximum observed temperature and a minimum observed temperature along the FO-DTS sediment dynamics monitoring device; calculate the temperature gradient of the observed temperature profile; determine a location of a sediment-water interface, wherein the location of the sediment-water interface corresponds to a location of a minimum temperature gradient observed between a lower end of the FO-DTS sediment dynamics monitoring device and the location of the minimum observed temperature; and determine a location of an air-water interface if the location of the maximum observed temperature being above the location of the minimum observed temperature, wherein the location of the air-water interface corresponds to a location of a maximum temperature gradient observed between the location of the minimum observed temperature and the location of the maximum observed temperature. The identified location of the interface can be a sediment-water interface or a water-air interface. The DTS system can be configured to determine water velocity about the FO-DTS scour monitoring device based at least in part upon the temperature profile. The DTS system can be configured to identify a location of a second interface along the length of the support structure based upon the temperature profile. The identified locations of the interfaces can comprise the sediment-water interface and the water-air interface. The DTS system can be configured to determine air velocity about the FO-DTS sediment dynamics monitoring device based at least in part upon the temperature profile. The DTS system can be configured to determine rate and amount of sediment movement about the FO-DTS sediment dynamics monitoring device based at least in part upon the temperature profile within the portion of the device buried within the sediment.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figures 1A, 1B:
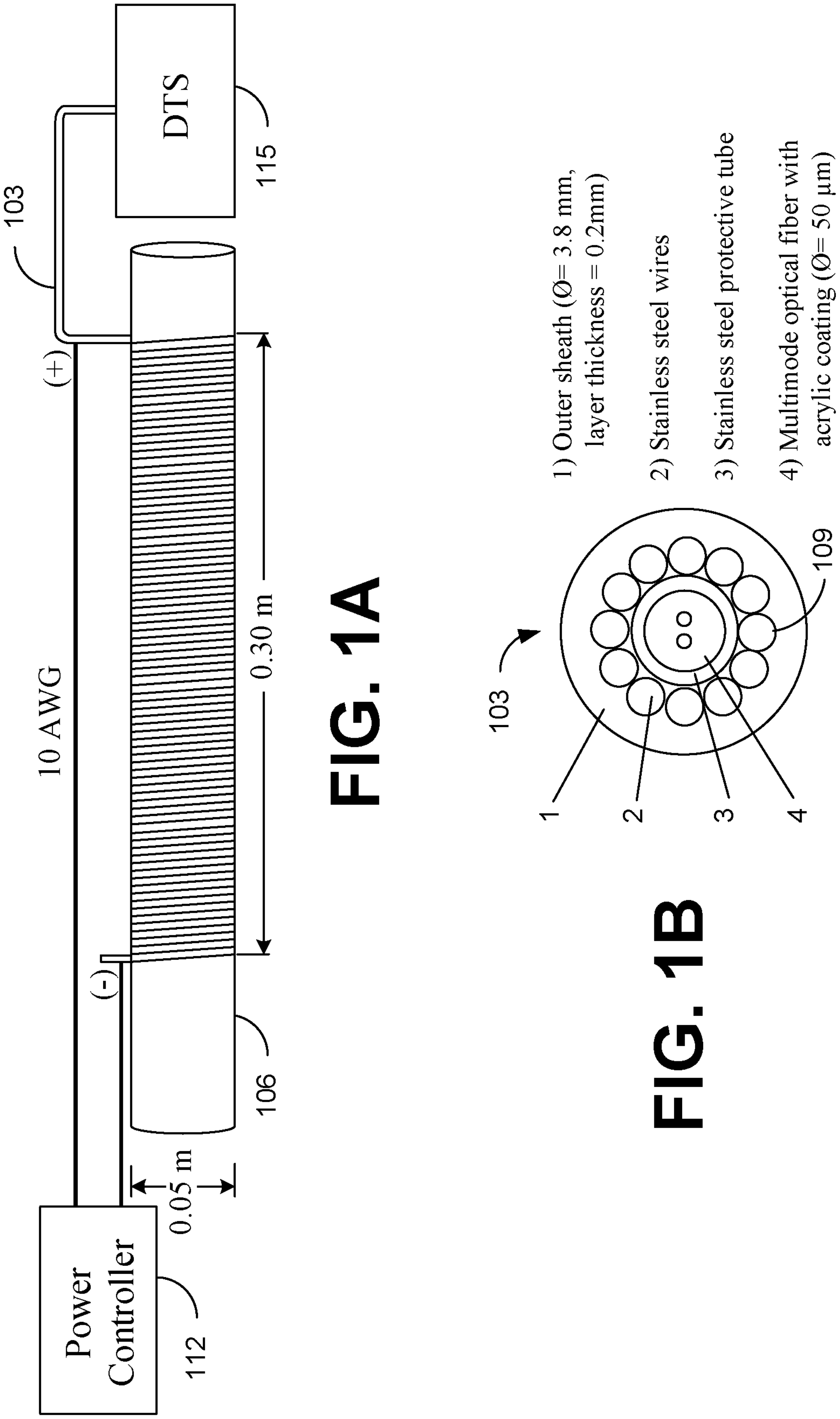
FIGS. 1A and 1B illustrate an example of a fiber-optic distributed temperature sensing (FO-DTS) sediment dynamics monitoring device, in accordance with various embodiments of the present disclosure.

Disclosed herein are various examples related to high-resolution scour and sediment erosion and deposition sensing including, e.g., water depth and/or water velocity sensing. The complex phenomena of sediment transport have great implications on the hydrology and geomorphology of any fluvial system, or any structures installed on them. Changes in the hydraulic conditions of a waterway can trigger sediment scouring or sediment deposition that can lead to significant changes in the waterway geomorphology. Additionally, local scouring around water structures can lead to their failure. For instance, scour is the leading cause of bridge failure in the United States. The Federal Highway Administration established the National Bridge Inventory (NBI) where States are required to report on the condition of public bridges. Structurally deficient or scour-critical bridges must be identified and a plan of action for monitoring and scour countermeasures must be developed. Obtaining a better understanding of the sediment scour phenomena necessitates the development of techniques capable of real-time monitoring of these phenomena with high temporal and spatial resolution. Reference will now be made in detail to the description of the embodiments as illustrated in the drawings, wherein like reference numbers indicate like parts throughout the several views.

Many techniques have been developed to monitor scour using buried-rods or float-out devices, using electromagnetic or sound pulses, or using strain mechanical devices. However, these techniques suffer from one or more of the following limitations: 1) inability of monitoring scour during flooding events when the extreme scouring typically occurs, 2) high-cost, low-durability, or high-maintenance requirements, 3) influenced by other environmental factors (e.g., temperature) leading to errors in the estimated scour depth, and 4) having low temporal or scour-detecting resolutions. A novel fiber-optic Distributed Temperature Sensing (FO-DTS) sediment dynamics monitoring device capable of tracking changes in the sediment-water interface at high spatial and temporal resolutions is disclosed which can provide the measurements needed to monitor scour events and the hydraulic conditions associated with these events.

The sediment dynamics monitoring device utilizes FO-DTS technology to dynamically monitor at sub-centimeter resolution changes in scour depth, water depth, water velocity, and temperature profiles from the water surface to the river bed or base/sediment of the waterway, including ocean, bay, stream, river, creek, pond or lake. It can also be utilized to monitor bank erosion and sediment transport in general. FIG. 1A illustrates an example of the sediment dynamics monitoring device comprising a fiber-optic (FO) temperature sensing cable 103 wrapped around a supporting structure 106 to increase the vertical sensing resolution of the sediment dynamics monitoring device. A heating element 109, that is collocated along the FO cable, applies heat at a constant (or controllable) rate along the sediment dynamics monitoring device when energized (e.g., via a connection cable) by a power controller 112. For example, the heating element 109 can be wrapped around the supporting structure 106 below the FO cable 103, wrapped next to the FO cable 103 around the supporting structure 106, or incorporated in the composition of the FO cable 103. If the FO cable 103 is installed in a fluvial system and heated using the heating element 109 (e.g., a metallic component), the increase in temperature observed using the distributed temperature sensing (DTS) 115 over the length of the FO cable 103 will depend on the thermal properties of the surrounding material and the strength of any convective cooling that exists.

The sediment dynamics monitoring device can be inserted vertically or horizontally or at any angle (e.g., in a range from 0 degrees to 90 degrees from normal to the water surface, or 0 degrees to 60 degrees from normal, or 0 degrees to 45 degrees from normal, or 0 degrees to 30 degrees from normal) in between in the river bed so that it is partially buried in the sediment, while the other sections of the sediment dynamics monitoring device are submerged in water or/and surrounded by ambient air. The changes in the thermal and convective cooling properties observed across the sediment-water and water-air interfaces will lead to anomalies in the observed temperature-increase profiles, which can be used to detect the locations of these interfaces. The sediment dynamics monitoring device utilizes the differential thermal responses of the sediment, water, and air media to a heating event to accurately identify the locations of the interfaces between them.

Changes in the thermal and convective cooling properties observed across the sediment-water and water-air interfaces lead to anomalies in the observed temperature-increase profiles, which can be used to detect the locations of these interfaces. By tracking the location of the sediment-water interface, scour and sedimentation along the sediment dynamics monitoring device can be identified. Identifying the location of the water-air interface allows a user to measure the water depth relative to the location of the sediment-water interface. Additionally, the variation of the thermal response along the submerged section of the sediment dynamics monitoring device may be attributed to the variability in water velocity as locations with higher water velocities show lower temperature increase. Similarly, the thermal response along the section that is exposed to air is a function of the wind velocity observed at each measurement point. The same approach can also be applied to reveal the location and the magnitude of sediment displacement along the buried section of the sediment dynamics monitoring device.

The sediment dynamics monitoring device can enable dynamic detection of sediment scour and deposition depths during the occurrence of storms, including the true maximum depth of the scouring. The sediment dynamics monitoring device can provide high temporal (e.g., every 5 minutes or over a range of intervals from about 1 minute to about 30 minutes or longer such as, for example, 1 minute, 2 minutes, 5 minutes, 10 minutes, 15 minutes, 20 minutes, 25 minutes, 30 minutes, or other intervals) and spatial (e.g., every 5 mm or a range of measurements from about 1 mm to about 50 mm or larger such as, for example, 1 mm, 2 mm, 3 mm, 5 mm, 7 mm, 8 mm, 10 mm, 25 mm, 50 mm or other dimensions) measurements of changes in sediment depths, water depths, and temperature profiles. Similar resolution may be achieved for measuring water velocities, wind velocities, and sediment movement. The sediment dynamics monitoring device can provide simultaneous measurements of sediment depths, water depths, water velocities, water temperatures, wind velocities, and sediment movement. No practical system, or combination of sensing systems, can provide the combination of these measurements with similar resolution or cost.

A single DTS system can be used to monitor sediment depths, water depths, water velocities, water temperatures, wind velocities, and/or sediment movement at multiple locations by connecting the DTS to one continuous FO cable wound in series around multiple supporting structures installed at the monitoring locations and each of them is equipped with a heating element collocated or integrated within the FO cable composition and connected to the power controller. Alternatively, the DTS system can be connected in parallel to independent devices; each of which comprises a separate FO cable wound around a supporting structure placed at one of the monitoring locations and equipped with a heating element collocated or integrated within the FO cable composition and connected to the power controller. It should be noted that devices connected in a combination of in parallel and in series can still be operated using a single DTS system.

The sediment dynamics monitoring device can be fabricated using off-the-shelf components, which can reduce the cost of material and fabrication. Both laboratory and field testing delivered consistent results regardless of the prevailing environmental conditions. The sediment dynamics monitoring device that was tested in the field proved to be durable and of low maintenance.

In the example of FIG. 1A, the FO-DTS sediment dynamics monitoring device can be constructed by tightly wrapping the FO cable 103 (e.g., a BRUsens® FO cable, Brugg cables, Switzerland) around the supporting structure 106. For example, the FO cable 103 can comprise 50 μm optical fibers encased within a gel-filled stainless steel tube (inner diameter 1.07 mm and outer diameter 1.3 mm) surrounded by 0.42 mm diameter stainless steel reinforcing wires and covered by a 0.83 mm nylon jacket as shown in FIG. 1B. It should be noted that if the heating is applied using an independent heating collocated with the FO cable, any commercial or custom manufactured FO cable with any diameters ranging from 0.01 cm (or 0.05 cm or 0.1 cm) to 5 cm or more can be used instead of the one described here. If the FO cable will be used to apply the heating, the used FO cable includes a heating element integrated in the FO cable design, which can be made of stainless steel, copper, silver, or any other electric-conductive material. When wound on the pipe, the FO cable 103 can extend along a total length of, e.g., 30 cm as shown in FIG. 1A. The length can be adjusted to accommodate the typical water depths encountered in a certain fluvial system. For example, the length of the wound FO cable 103 can range from, e.g., about 15 cm to about 10000 cm or more depending on the application. For instance, the length can total length of the wound FO cable 103 can be 20 cm, 30 cm, 40 cm, 50 cm, 60 cm, 70 cm, 80 cm, 90 cm, 100 cm or other lengths as needed for the application. In that design, every one vertical centimeter along the sediment dynamics monitoring device is represented by 0.54 m along the FO cable 103. The size of the supporting structure and the diameter of the used FO cable can be varied to adjust resolution of the sensing. The size of the supporting structure can be selected to provide sufficient support for the sediment dynamics monitoring device while also considering its effect on the flow around the device. The supporting structure has a length that is sufficient to extend beyond the ends of the wound FO cable 103 and can have a diameter in a range, e.g., from about 2.5 cm to about 25 cm (for example, 2.5 cm, 5 cm, 7.5 cm, 10 cm, 15 cm, 20 cm or other diameters). The heating element 109 can include the stainless steel tube and/or reinforcing wires extending through the FO cable 103, or can be a separate metallic component covered by any electrical insulator that is collocated with the FO cable 103 on the supporting structure 106.

A DTS system 115 (e.g., Silixa XT®, Silixa Ltd, UK) with sampling and temporal resolutions of 0.25 meter and 5 seconds can be used to monitor the temperature over the whole length of the FO cable 103. Any other DTS system from any manufacturer can be used and the characteristics of the sediment dynamics measuring device can be adjusted to the DTS spatial and temporal resolution. An internal calibration algorithm can be used to measure the temperature profiles of the sediment dynamics monitoring device. To achieve active heating of the FO cable 103, the stainless steel tube and/or wires integrated within the FO cable 103 can be used as the heating element 109 by connecting them to a power controller 112 (e.g., a BK Precision 9205 DC power supply, B&K Precision Corp., USA).

An algorithm (e.g., using Matlab, MathWorks, 2020) can be used to automatically identify the location of the air-water and sediment-water interfaces. The input to the algorithm can be the average temperature profile obtained over the heat pulse duration (e.g., 5 minutes or over a range of durations from about 30 seconds to about 1000 seconds or longer such as, for example, 60 seconds, 120 seconds, 180 seconds, 300 seconds, 400 seconds, 600 seconds, 750 seconds, 900 seconds, or other intervals). The optimal heat pulse duration for a certain application can be defined based on the needed accuracy in the detected interfaces and the frequency at which the changes in these interfaces need to be measured. The algorithm can compute the temperature gradient and identify the locations of the air-water and sediment-water interfaces as those locations associated with the maximum and the minimum temperature gradients, respectively.

Minimizing the duration of the measurement while maintaining appropriate measurement accuracy can allow higher frequency readings of the scour location. The performance of the FO-DTS sediment dynamics monitoring device in terms of detecting the location of the interfaces can be evaluated for measurement durations ranging from about 5 seconds to about 600 seconds with 5 second increments (the DTS measuring interval). This can be achieved by averaging the DTS measurements observed over the measurement duration starting from initiation of the FO heating and using the averaged signal to detect the sand-water and water-air interfaces.

The performance of the FO-DTS sediment dynamics monitoring device was initially tested in a laboratory flume under different flow conditions. In addition, the effect of the measurement duration on the device measurement accuracy was also examined.

Flume Description

Figure 2:
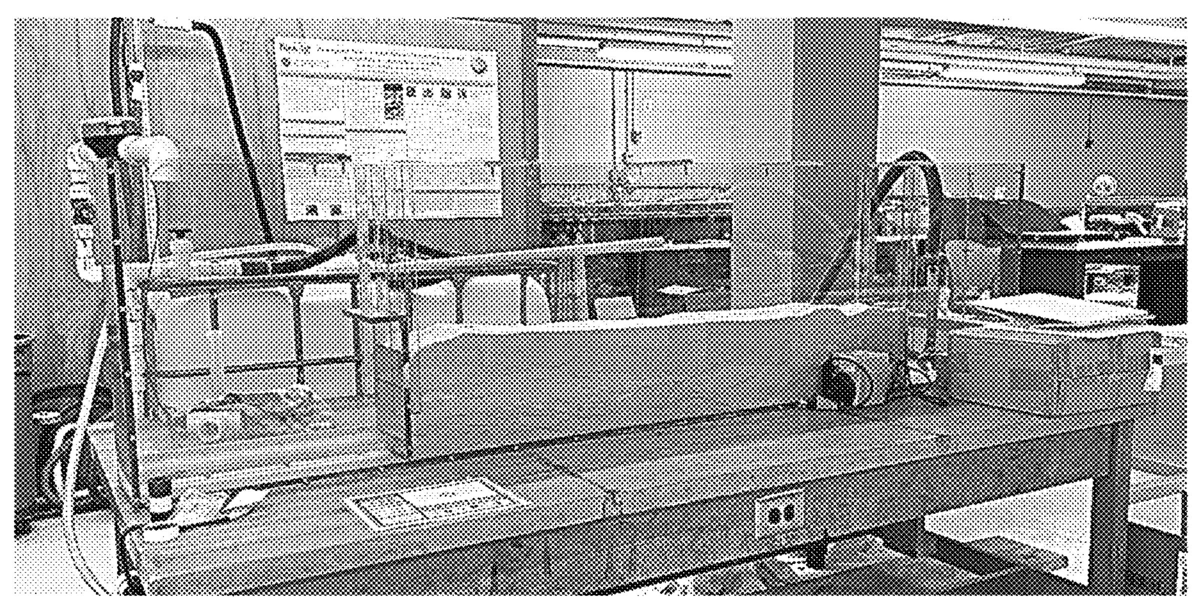
FIG. 2 is an image of a flume used to test FO-DTS sediment dynamics monitoring devices, in accordance with various embodiments of the present disclosure.

In order to test the performance of the FO-DTS sediment dynamics monitoring devices under varying flow and sediment depth conditions, an experimental flume was constructed. FIG. 2 is an image of the flume used for the testing. The 2.4 m long by 0.2 m wide by 0.6 m tall flume was used for all laboratory testing of the FO-DTS sediment dynamics monitoring devices. Water was pumped out of a reservoir and into the inlet chamber of the flume through a series of PVC pipes and valves. Water then filled the inlet box before flowing over an L-shaped divider into the testing section of the flume. Dividers that were 7.6 cm tall were stacked on top of each other to adjust the height of sediment in the testing section. Water then flowed through the testing section and to the outlet chamber. The water drained through a hose to a small pool and was pumped back to the reservoir to recirculate water. A flow meter was installed in the PVC pipes coming into the inlet box, so a stage-discharge relationship could be made for the flume. The stage was measured by recording the depth of water over the L-shaped divider flowing into the testing section.

FO-DTS Sediment Dynamics Monitoring Device Description

Figure 3A:
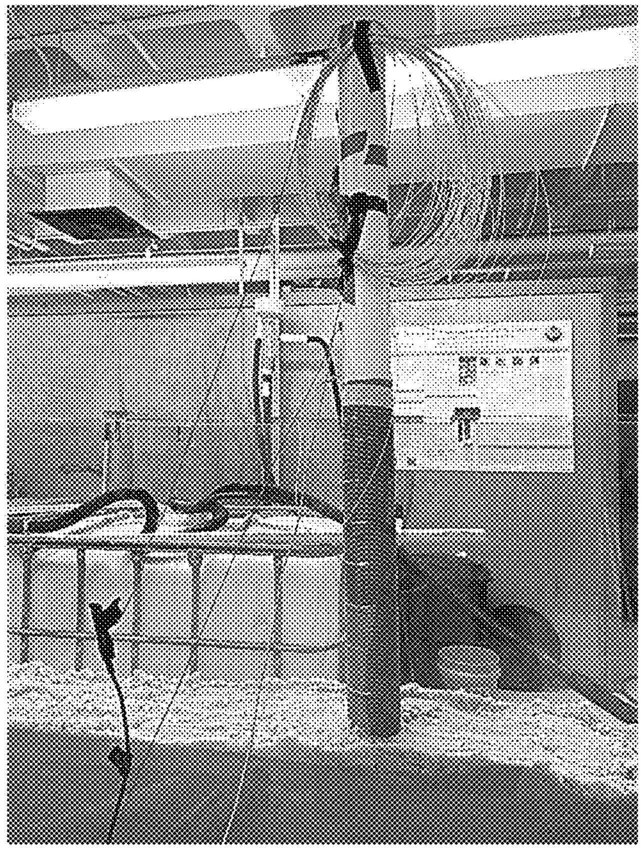
FIGS. 3A and 3B are images of examples of FO-DTS sediment dynamics monitoring device prototypes, in accordance with various embodiments of the present disclosure.

Two prototypes of the FO-DTS sediment dynamics monitoring device were constructed to test the FO-DTS's ability to locate and track the sediment-water interface. FIG. 3A is an image of the first prototype (prototype 1) that was constructed by wrapping a FO cable around a 5 cm diameter pipe that was used as the supporting structure. Prototype 1 had a diameter of 50.8 mm and a height of 0.6 m (60 cm). The FO cable chosen for this device had an outer diameter of 0.9 mm and contained a multi-mode optical fiber without a heating element. To be able to perform an active heating test, the heating cable was then wrapped on top of the FO cable. A 20 AWG heating cable sheathed in silver plated copper, with an outer diameter of 0.058 in. (Remington Industries, USA), was wrapped on top of the FO cable.

Figure 3B:
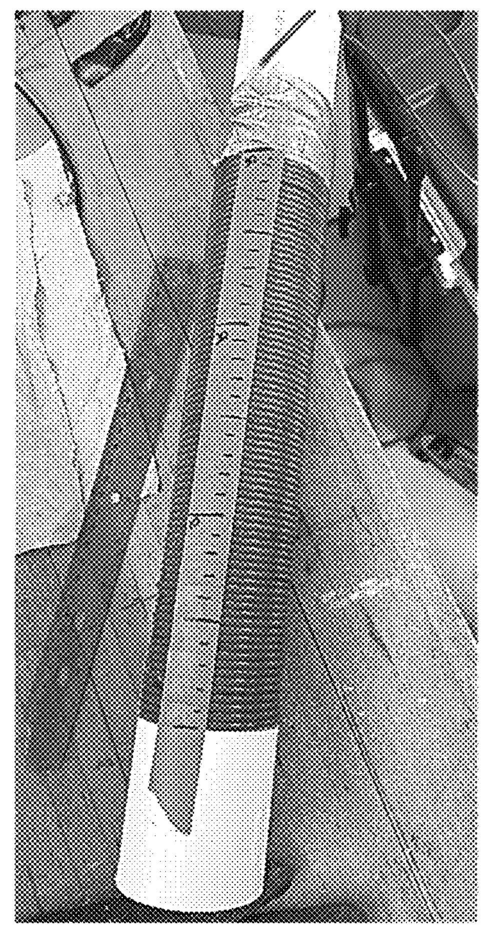

FIG. 3B is an image of the second prototype (prototype 2) that was constructed by wrapping a FO cable around a 5 cm diameter PVC pipe as illustrated in FIG. 1A. The cable chosen was the BRUsens® (Brugg cables, Switzerland) FO cable which comprises an inner multimode FO filament as well as stainless steel wires that can act as a heating element as shown in FIG. 1B. The wrapped section of cable was 30 cm tall, along the PVC pipe. The second prototype sediment dynamics monitoring device was placed in the sand in the same manner as the first prototype sediment dynamics monitoring device and the calibration bath temperatures were also the same.

In each test of the sediment dynamics monitoring device, it was placed vertically in the flume, so that part of it was buried under sand ($D_{50}$ of 0.15 mm), part of it was exposed directly to water, and another section was only exposed to the air. The FO cable that was wrapped around the supporting structure was also connected to a DTS machine and coiled in two calibration baths. One calibration bath was kept at room temperature water and the other had a 0° C. ice-water slurry mix. Two different DTS machines were used for these experiments. The Silixa Ultima® (Silixa Ltd, UK) with a sampling resolution of 0.125 m every 1 second and a spatial resolution of 0.25 m was used in the testing of prototype 1. Prototype 1 had a vertical resolution of 1.92 m for every 1 cm vertically along the device. The Silixa XT® (Silixa Ltd, UK) with a sampling resolution of 0.25 m every 5 seconds, a spatial resolution of 0.5 m every 5 seconds was used for prototype 2. Prototype 2 had a vertical resolution of 0.54 m for every 1 cm vertically along the device.

To achieve active heating of the FO cable, a copper wire attached to the BK Precision 9205 600 W DC power supply was spliced to the heating element of the sediment dynamics monitoring device at both ends (B&K Precision Corp., USA). For each test, the power supply was controlled to heat the cable with approximately 60 V and 7 A for two to five minutes. These values were the maximum power that could be supplied in the experimental setup without tripping the power supply.

Experiment Design

During the first tests of prototype 1, no scour was created, and the prototype was used to capture the static sand-water interface at three different flow velocities. The average velocities were 2.7 cm/s (hereafter high flow), 0.59 cm/s (hereafter low flow), and standing water (hereafter zero flow). In the subsequent tests, scour was simulated by pulling the sediment dynamics monitoring device out of the sand bed. The latter tests were performed to track changes in the location of the sediment-water interface and to determine if these changes could be captured by the FO-DTS sediment dynamics monitoring device.

Prototype 2 was tested under various conditions in the flume ranging from zero to high flow. Flow was adjusted using the series of valves controlling the flow into the flume. The initial flow of water coming into the flume created erosion around the FO-DTS sediment dynamics monitoring device, but the bed level stayed relatively constant during the remainder of the experiment. Before the start of each experiment, the bed was smoothed and leveled to be the same in each run and the water was run through the flume for at least 30 minutes to reach thermal and hydraulic equilibrium.

An interface identification method was implemented in Matlab (MathWorks, 2020) to automatically identify the change of location of the air-water and sediment-water interface was developed to facilitate laboratory and field data processing from the FO-DTS sediment dynamics monitoring devices. The interface identification method uses the recorded temperature gradient along the FO-DTS sediment dynamics monitoring device to detect the interfaces as follows: (a) detect the locations of the maximum and minimum observed temperatures along the FO-DTS sediment dynamics monitoring device; (b) if the location of the minimum temperature is higher than the maximum temperature then the device is totally submerged underwater and the process will only detect a sediment-water interface; (c) calculate the gradient of the observed temperature profile; (d) find the location of the sediment-water interface, which corresponds to the location of the minimum temperature gradient observed over the device segment extending from the device end located inside the sediment and up to the location of the minimum observed temperature detected in the first step; (e) if the device is not submerged, find the location of the air-water interface that corresponds to the location of the maximum temperature gradient observed over the device segment between the locations of minimum and maximum temperatures detected in the first step.

Field Installation

Figure 4:
FIG. 4 is an image of installed FO-DTS sediment dynamics monitoring devices, in accordance with various embodiments of the present disclosure.

A field setup at the bridge crossing of Glenn Rd over Ellerbe Creek in Durham, NC was installed. FIG. 4 is an image of the field setup of two FO-DTS sediment dynamics monitoring devices at Ellerbe Creek. The field devices have the same design and material as prototype 2 but with a larger sensing length of 90 cm. In the setup, the FO-DTS sediment dynamics monitoring devices were connected to an additional PVC pipe that did not have any cable wrapped around it and that pipe was secured to the pier using super struts and ratchet straps. FIG. 4 shows the additional PVC pipe extending from the top end of the installed FO-DTS sediment dynamics monitoring device. Just like in the lab setup, the FO-DTS sediment dynamics monitoring device was partially buried in the sediment and the rest was under water on the day of the installation. Ideally, one sediment dynamics monitoring device would be on each pier, but due to the large amount of debris on the upstream pier both devices were placed on the downstream pier. The FO-DTS sediment dynamics monitoring devices were electrically connected in parallel and both the FO cable and a 12-gauge 150 ft electric cable were suspended over the stream and attached to a metal rod on the left bank.

Prototype 1 Laboratory Results

A total of four experiments were conducted to evaluate prototype 1. The high, low, and zero flow tests were all static scour tests i.e., the bed level remained constant throughout each test and there was no visible sediment transport taking place around the FO-DTS sediment dynamics monitoring device itself. In the scour-inducing test, the bed level itself did not change, but the placement of the prototype device in the sediment did change, so that the bed was at a different location along the FO-DTS sediment dynamics monitoring device. Because it was assumed that the bed level remained constant throughout the experiments, the sand-water interface was only measured once during the first three tests and then measured once after the prototype device was pulled out of the sand.

Figure 5A:
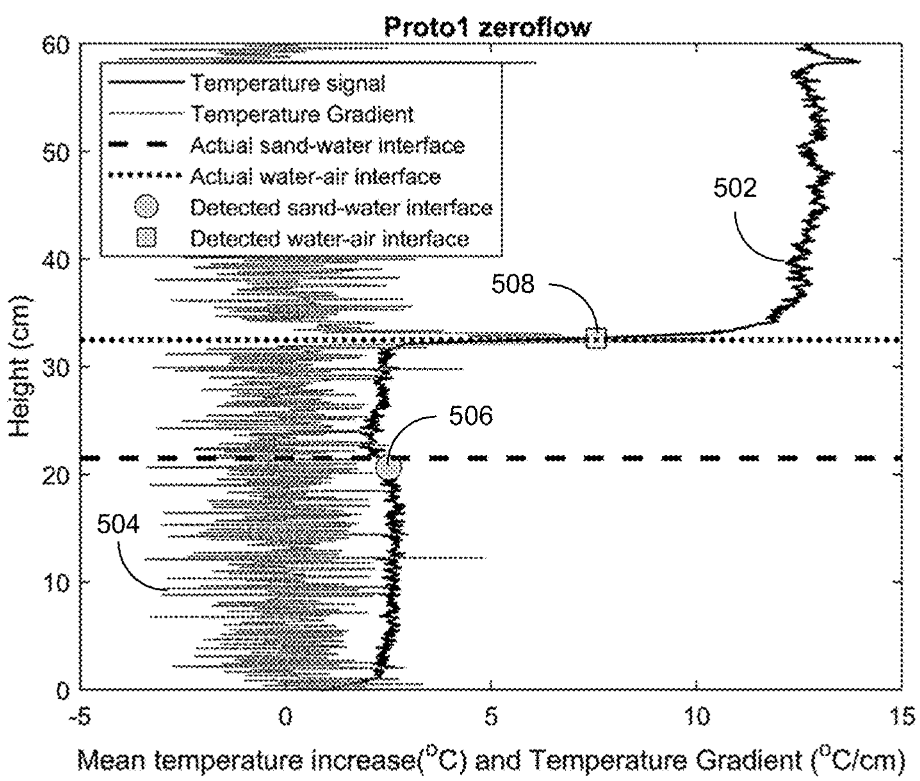
FIGS. 5A-5H illustrate examples of testing results of a first FO-DTS sediment dynamics monitoring device prototype, in accordance with various embodiments of the present disclosure.

In the no flow test, water was ponded in the flume while the cable was heated to determine if even under no flow conditions the sediment-water and air-water interfaces could be accurately detected by the FO-DTS sediment dynamics monitoring device. The results after five minutes of heating can be seen in FIG. 5A. The x-axis represents both the mean temperature increase (502) and the temperature gradient (504) observed along the cable while the y-axis is the vertical distance along the prototype. The vertical distance of zero represents the bottom of the prototype which was fully buried under sediment. The circle marker (506) represents the calculated sediment-water interface, and the square marker (508) marks the calculated water-air interface. The horizontal dashed and dotted lines represent the location of the independently measured sand-water and water-air interfaces respectively.

Figure 5B:
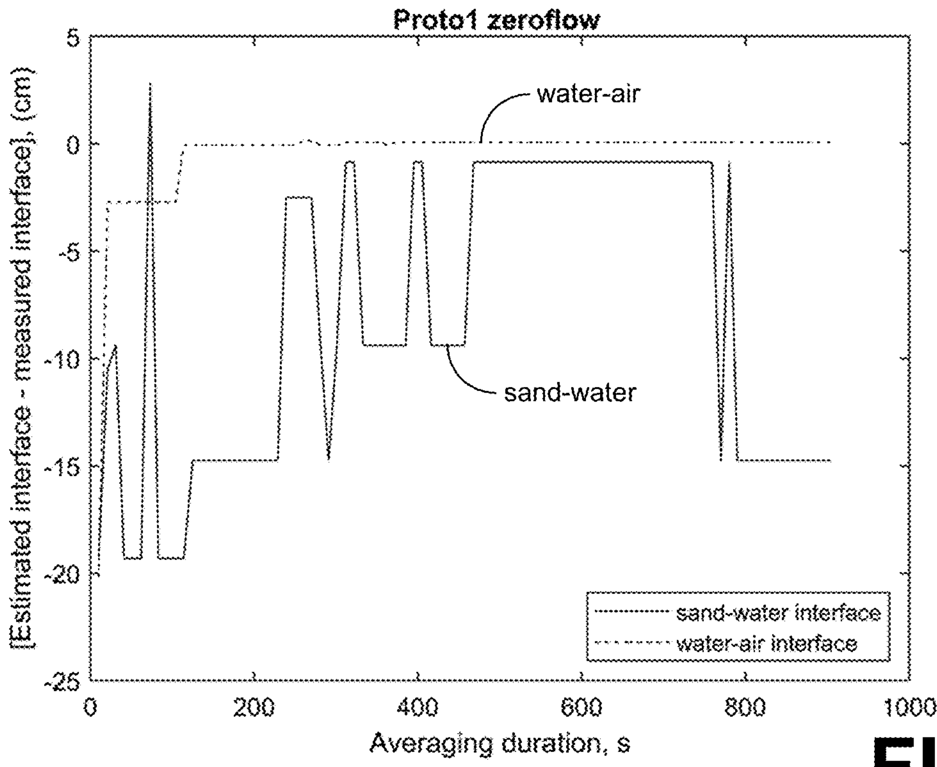

The error of the interfaces at various heating times was also analyzed to determine if heating time had an impact on the result and to identify the minimum heating time needed to accurately detect the location of the interface. FIG. 5B illustrates an example of the error of interface locations versus heating duration under zero flow for prototype 1. The analysis results showed that error in locating the interface decreased as time progressed and stabilized between 500 and 800 seconds after the heating started.

Figure 5C:
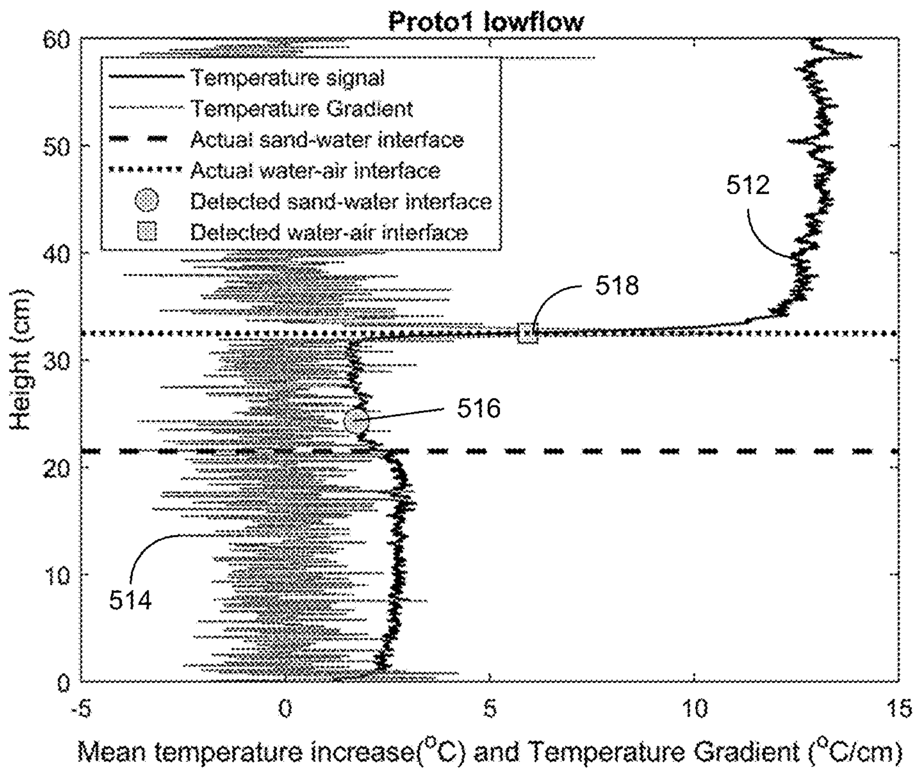
Figure 5D:
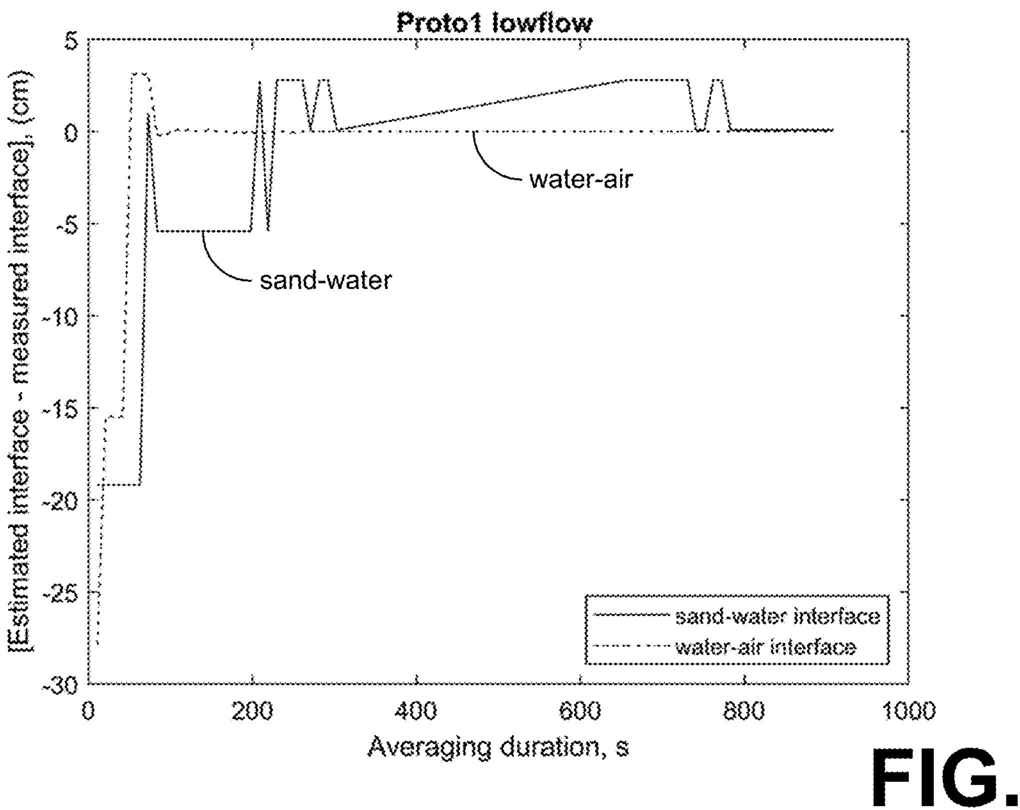

FIG. 5C illustrates the results after five minutes of heating for the low flow condition for prototype 1. The x-axis represents both the mean temperature increase (512) and the temperature gradient (514) observed along the cable while the y-axis is the vertical distance along the prototype. The vertical distance of zero represents the bottom of the prototype which was fully buried under sediment. The circle marker (516) represents the calculated sediment-water interface, and the square marker (518) marks the calculated water-air interface. The horizontal dashed and dotted lines represent the location of the independently measured sand-water and water-air interfaces respectively. In this condition, water flowed through the flume, but no scour was observed near the sediment dynamics monitoring device. FIG. 5D illustrates an example of the error of interface locations versus heating duration under low flow for prototype 1. Similar to the zero-flow condition, the error in locating the interface decreased as heating time increased and stabilized after 300 seconds with residual error around 2 cm.

Figure 5E:
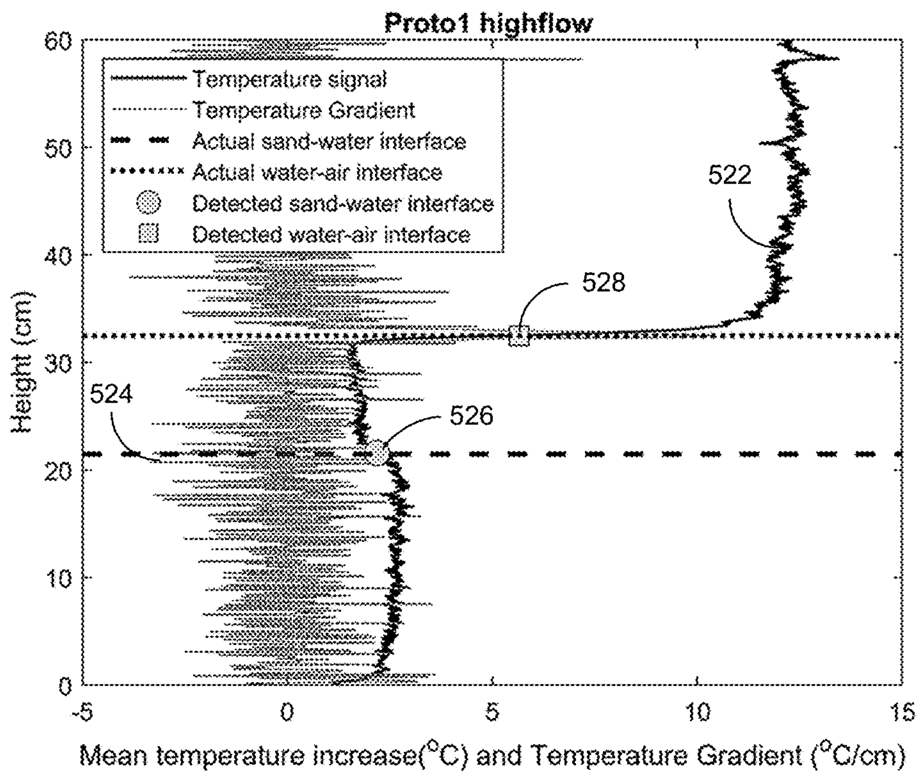
Figure 5F:
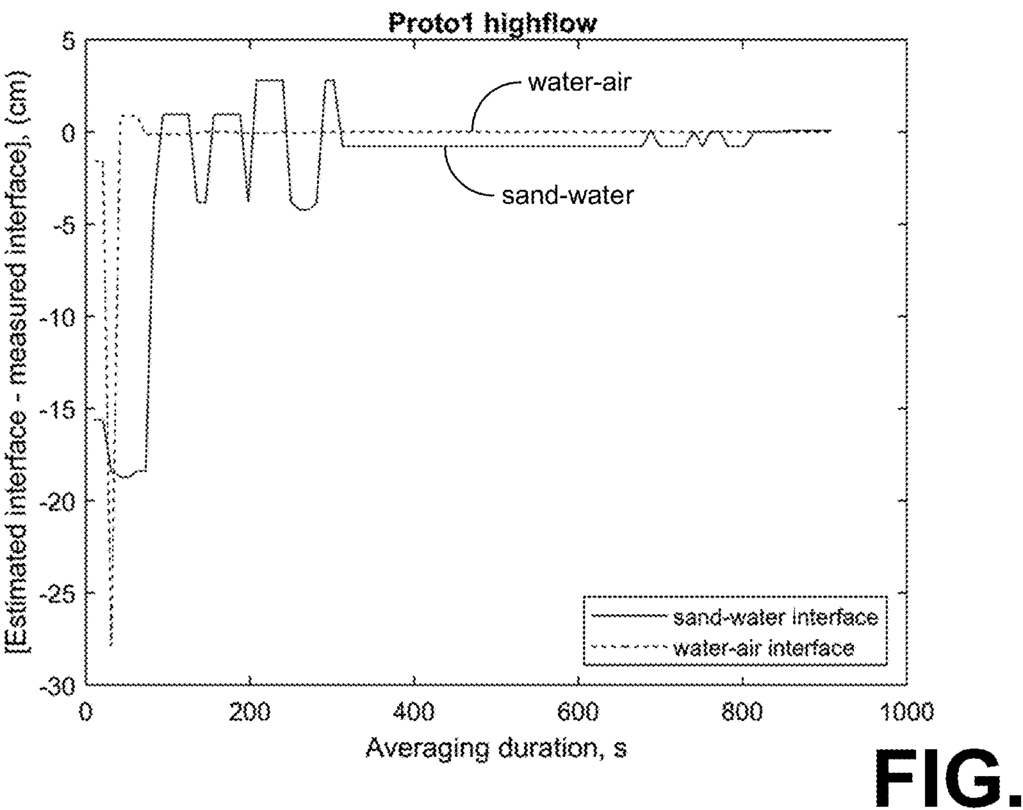

In the high flow condition, once again no scour was created around the FO-DTS sediment dynamics monitoring device. FIG. 5E illustrates the results after five minutes of heating for the high flow condition for prototype 1. The x-axis represents both the mean temperature increase (522) and the temperature gradient (524) observed along the cable while the y-axis is the vertical distance along the prototype. The vertical distance of zero represents the bottom of the prototype which was fully buried under sediment. The circle marker (526) represents the calculated sediment-water interface, and the square marker (528) marks the calculated water-air interface. The horizontal dashed and dotted lines represent the location of the independently measured sand-water and water-air interfaces respectively. The error over heating duration was also evaluated and the error of interface locations versus heating duration shown in FIG. 5F. The error stabilized around 300 seconds after the start of heating.

Figure 5G:
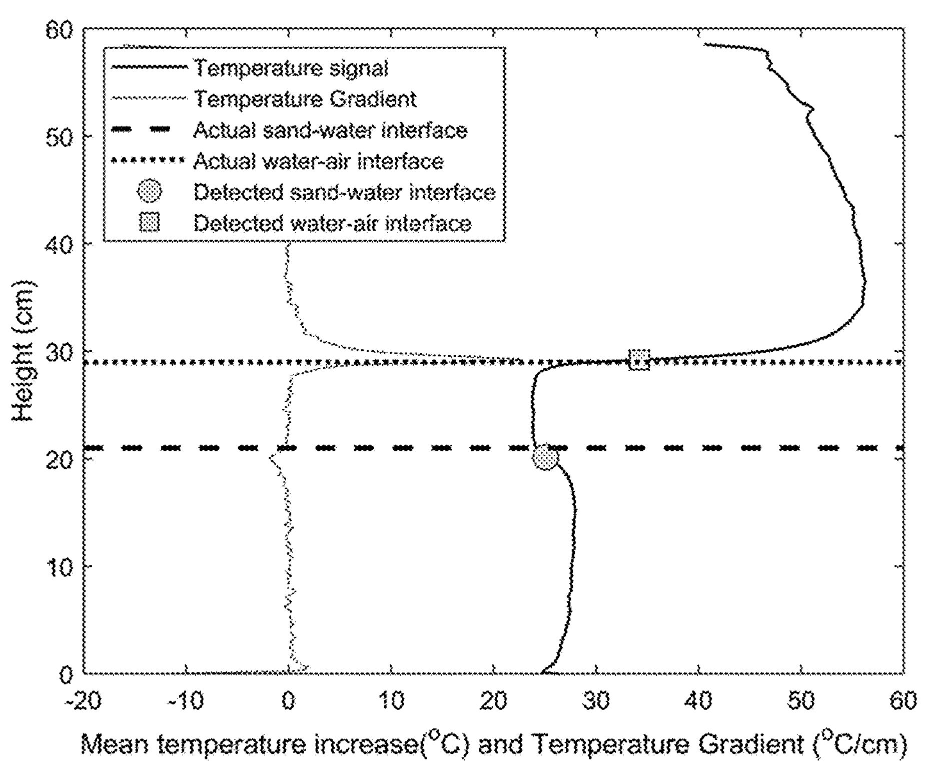
Figure 5H:
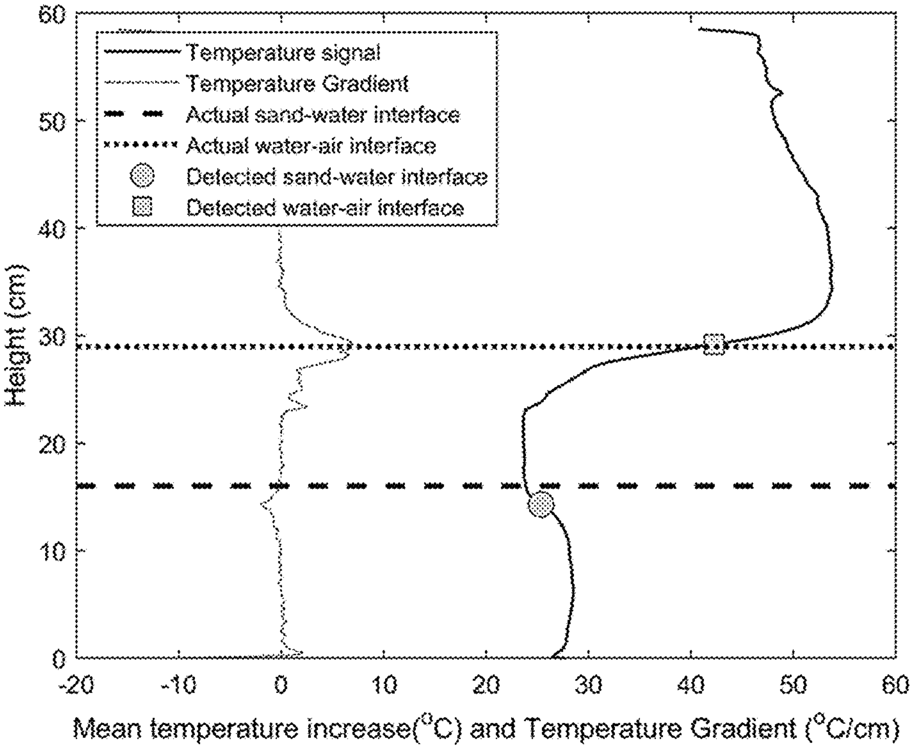

The last test of prototype 1 was a scour-inducing experiment in which the prototype device was vertically raised 5 cm to represent scour taking place around the FO-DTS sediment dynamics monitoring device. FIGS. 5G and 5H show the before and after plots of the sediment-water and water-air interfaces in the scour-inducing experiment. FIG.

5G contains the interfaces calculated before the sediment dynamics monitoring device was pulled out of the sediment and FIG. 5H contains the after the "scour" was simulated. Note that the sediment-water interface in the before image was located at 21 cm and after the sediment dynamics monitoring device was raised 5 cm the interface was located at 16 cm, a difference of 5 cm. The error of sediment interface location versus heating time could not be calculated in this experiment because of the way the FO-DTS sediment dynamics monitoring device was pulled out of the sediment.

The average error across all tests in identifying the sediment-water interface was 1 cm and the average time needed to accurately locate the interface was about 340 seconds.

Prototype 2 Laboratory Results

A series of nine total tests were performed to evaluate prototype 2 with three tests being from each condition (no flow, medium flow, and maximum flow). Water temperature was recorded in each of the tests and remained constant at 21° C. Both the no flow and medium flow conditions were static scour tests. Meaning that once scour was initially created around the sediment dynamics monitoring device, there was no following evolution of the scour hole. In the maximum flow tests, however; the height of the downstream barrier was removed as mentioned previously to increase velocity thus creating slight scouring.

Figure 6A:
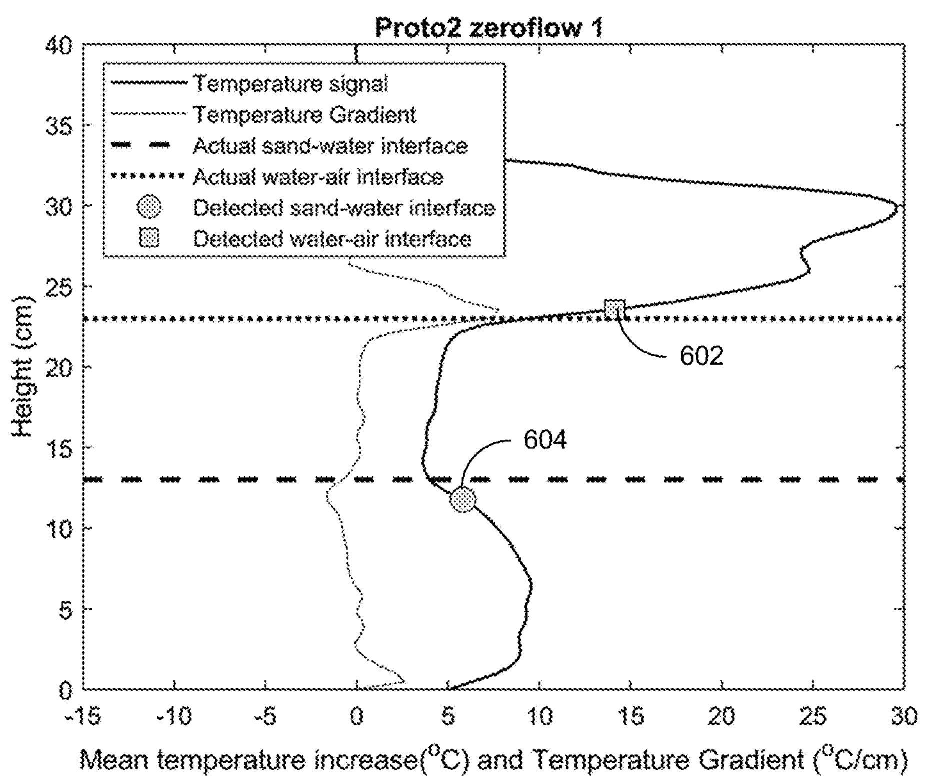
FIGS. 6A-6F, 7A-7F and 8A-8F illustrate examples of testing results of a second FO-DTS sediment dynamics monitoring device prototype, in accordance with various embodiments of the present disclosure.
Figure 6B:
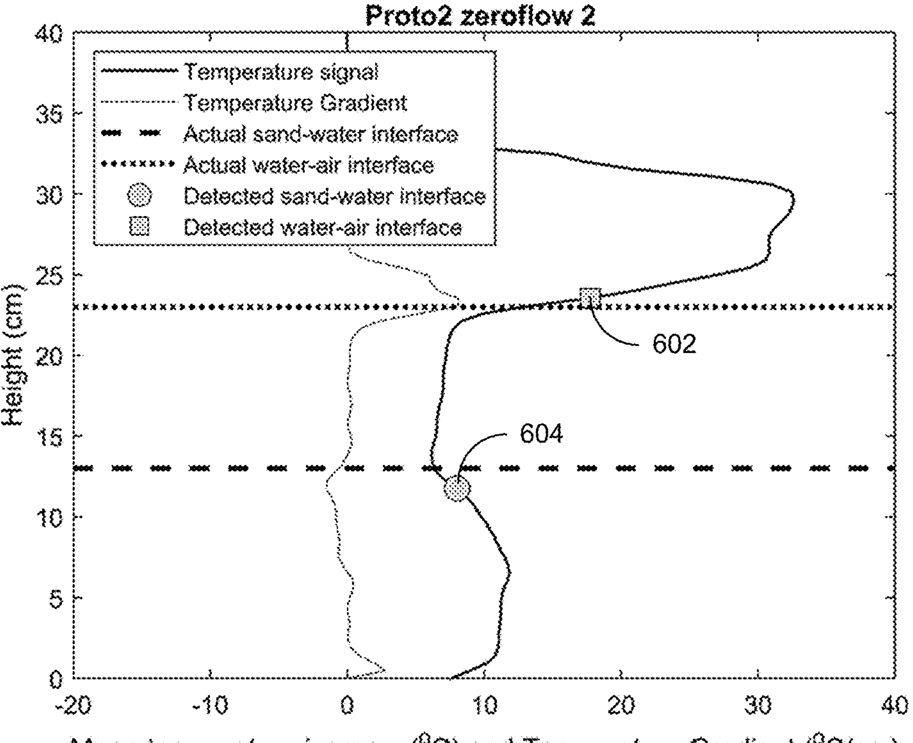
Figure 6C:
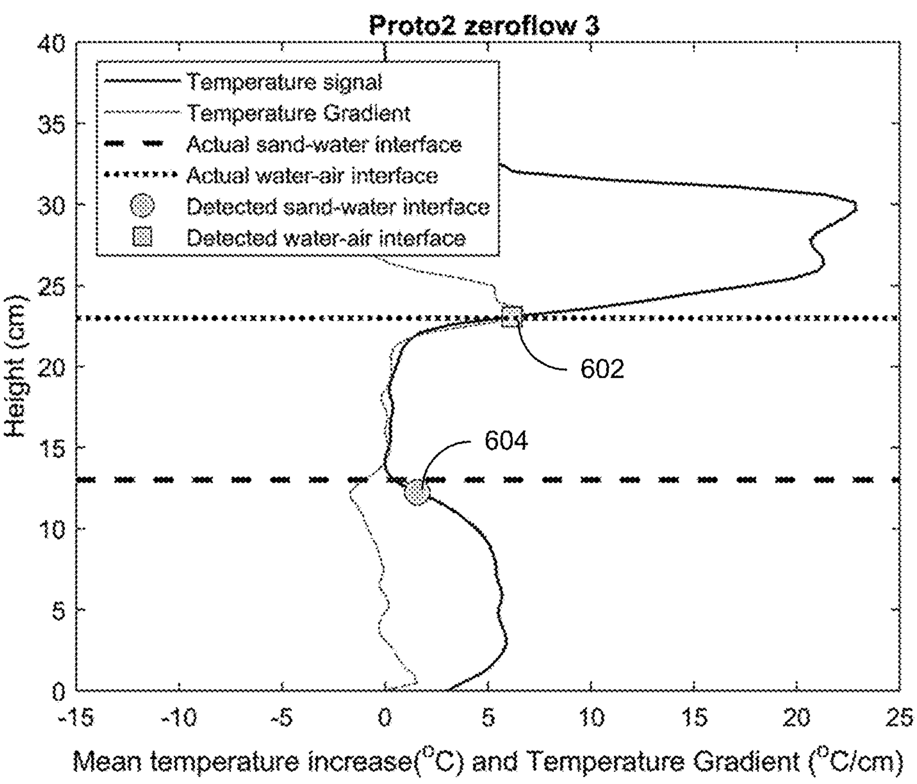
Figure 6D:
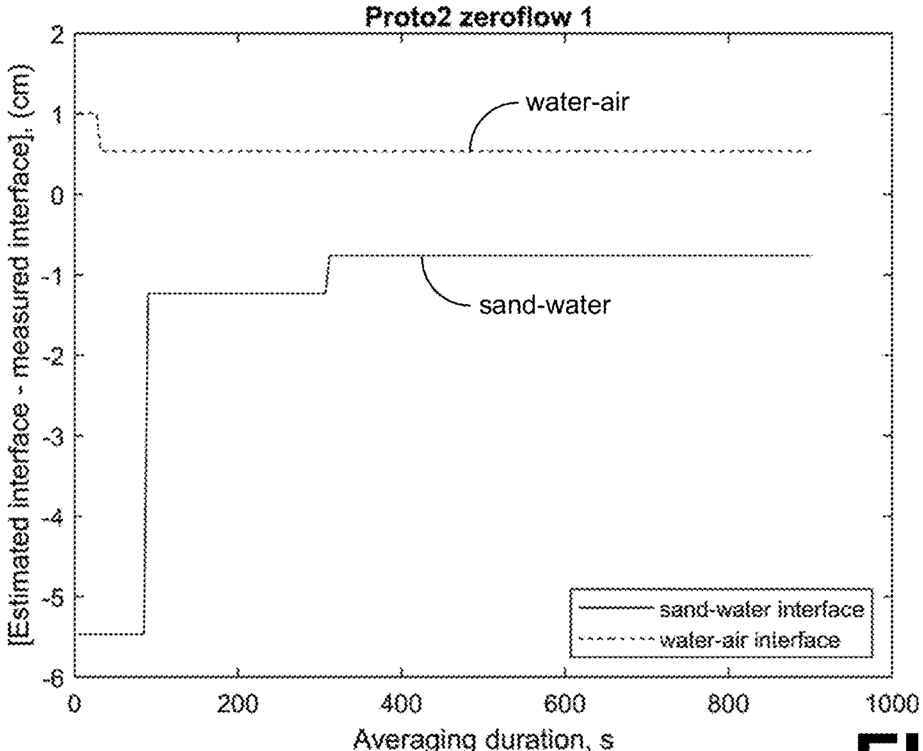
Figure 6E:
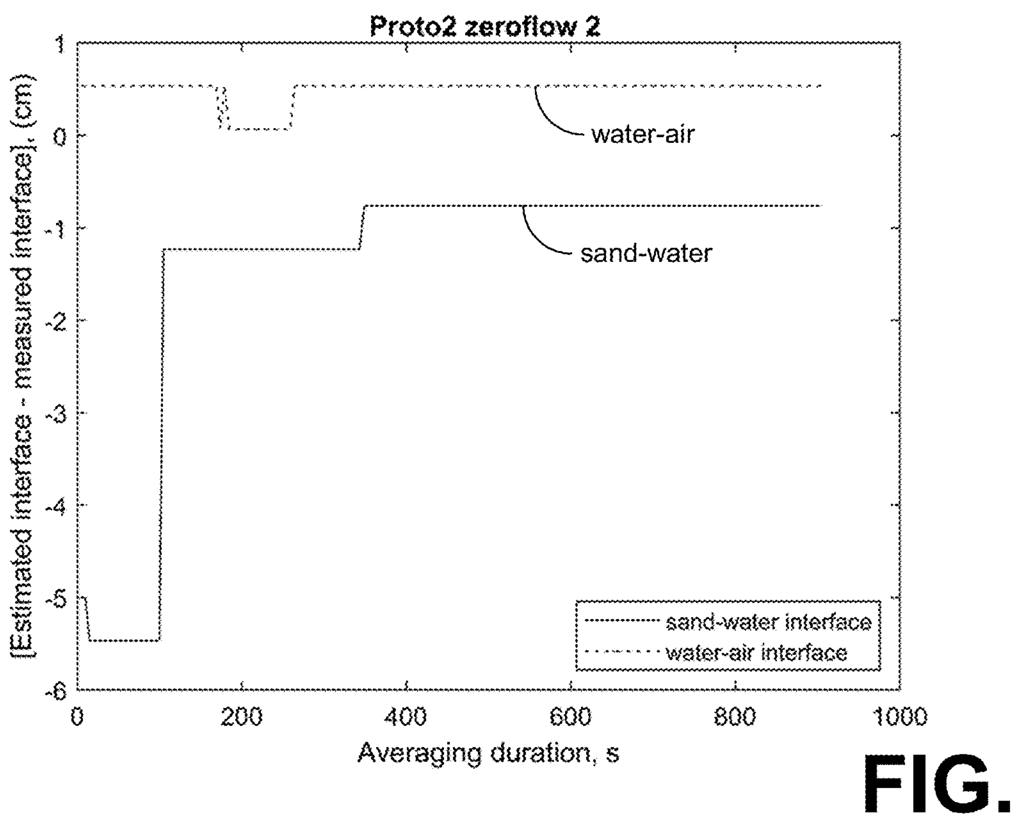
Figure 6F:
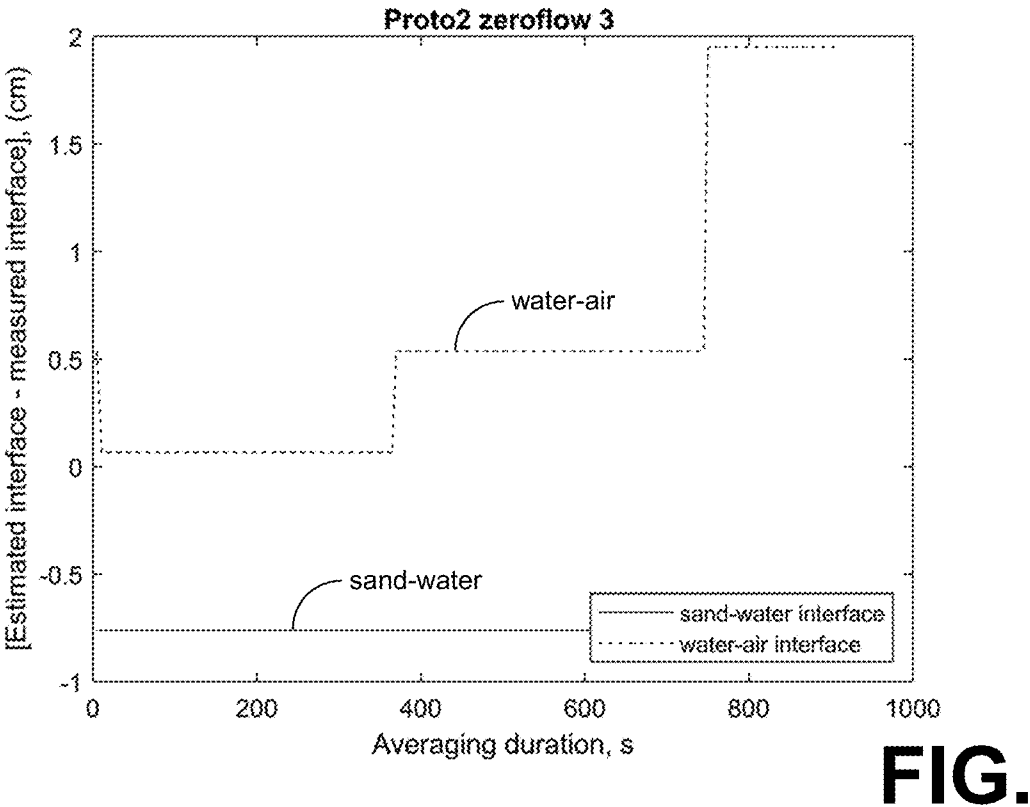

In the no flow tests, water was ponded at a depth of 9 cm above the sand. FIGS. 6A-6C illustrate results of the no flow tests for three heat pulses. The x-axis is the mean temperature increase and the temperature gradient, and the y-axis is the height of the device in centimeters. The circle marker (602) represents the sand and water interface. The square marker (604) represents the water-air interface, and the difference between the two stars was the water depth. Error can be explained by two factors: (a) measurement errors; (b) the vertical resolution of the prototype. Note that the algorithm used to detect the location of the interfaces has not been calibrated. Further refinement and calibration of the algorithm is expected to reduce this error. As with prototype 1, the error over heating time was analyzed for all tests of prototype 2. The error stabilized around 100 seconds of heating time. FIGS. 6D-6F illustrate the associated error versus heating time increments for the no flow tests.

Figure 7A:
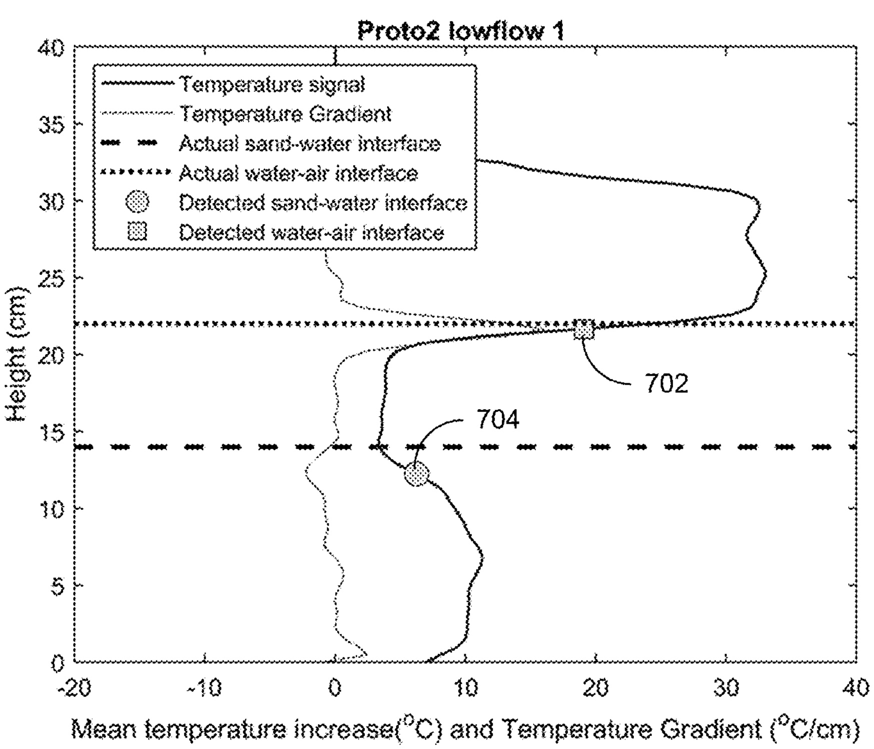
Figure 7B:
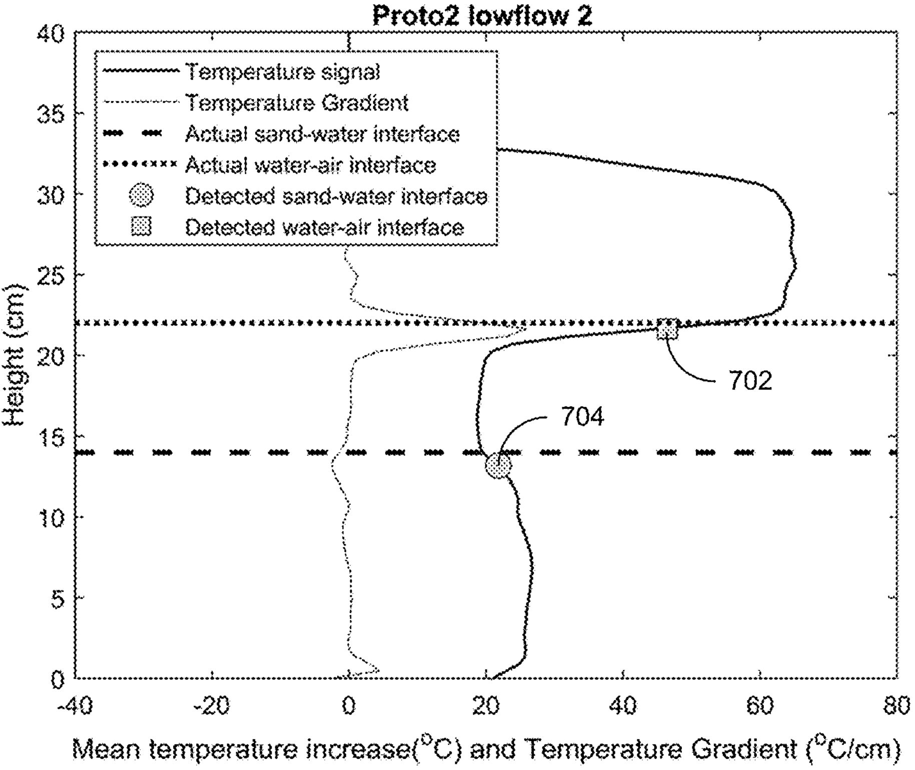
Figure 7C:
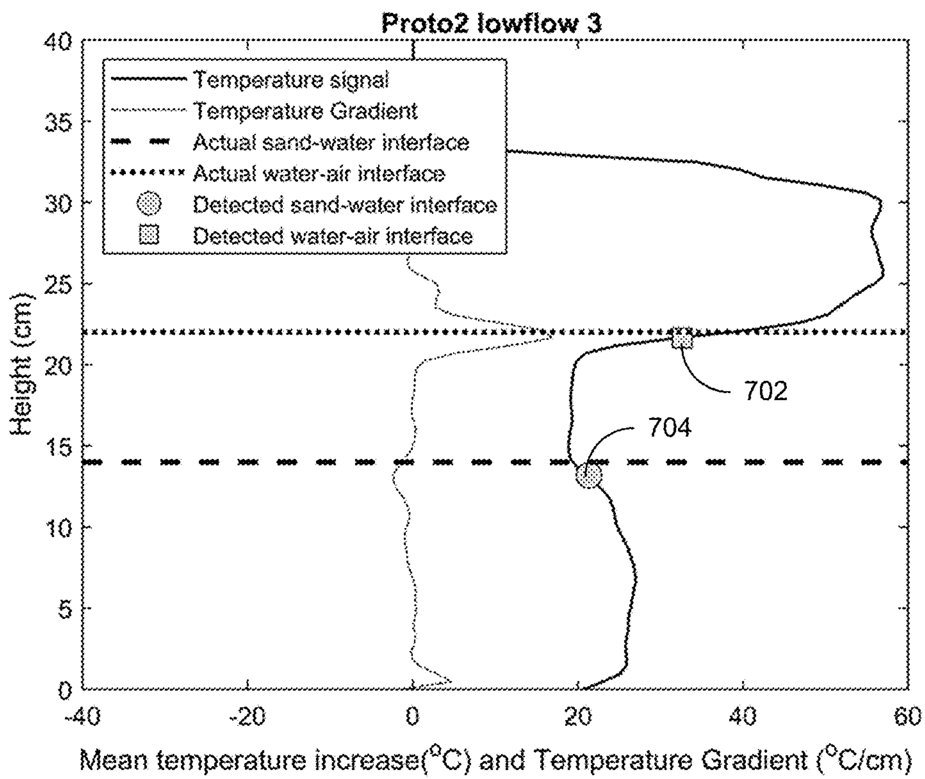
Figure 7D:
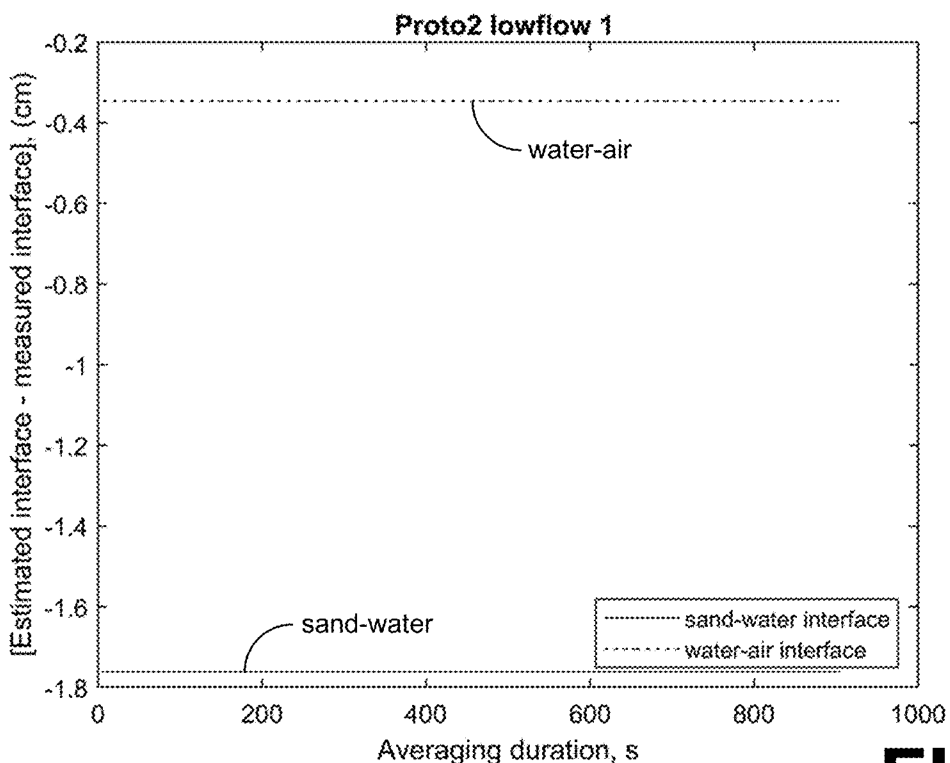
Figure 7E:
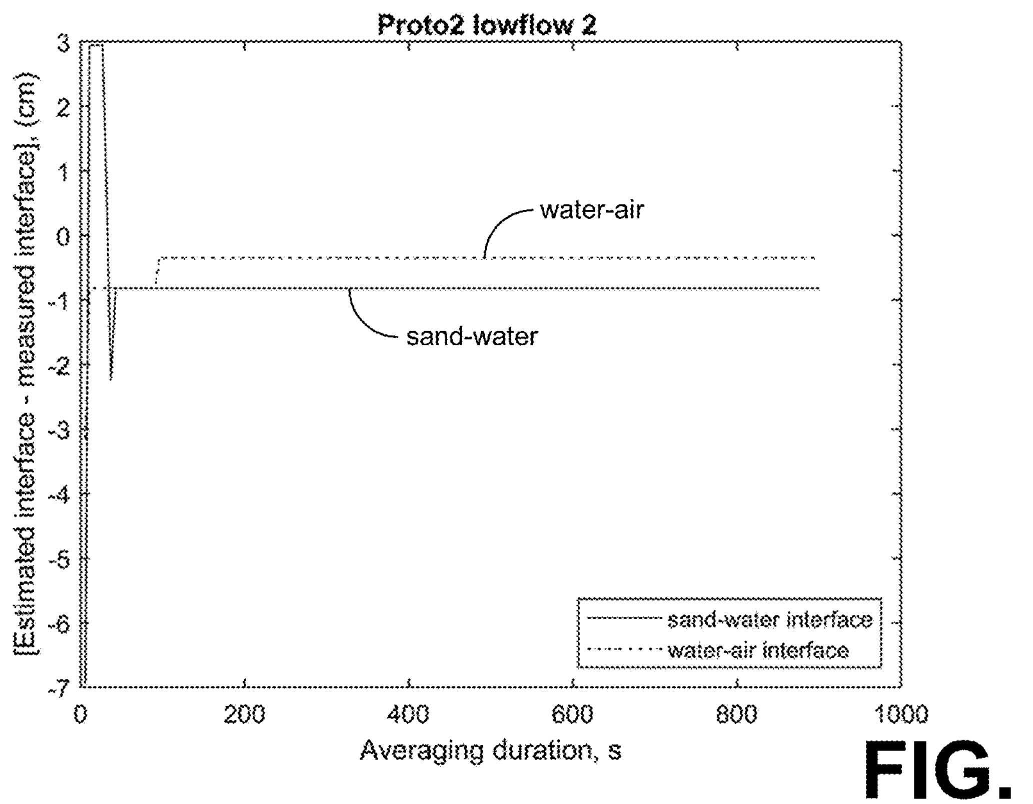
Figure 7F:
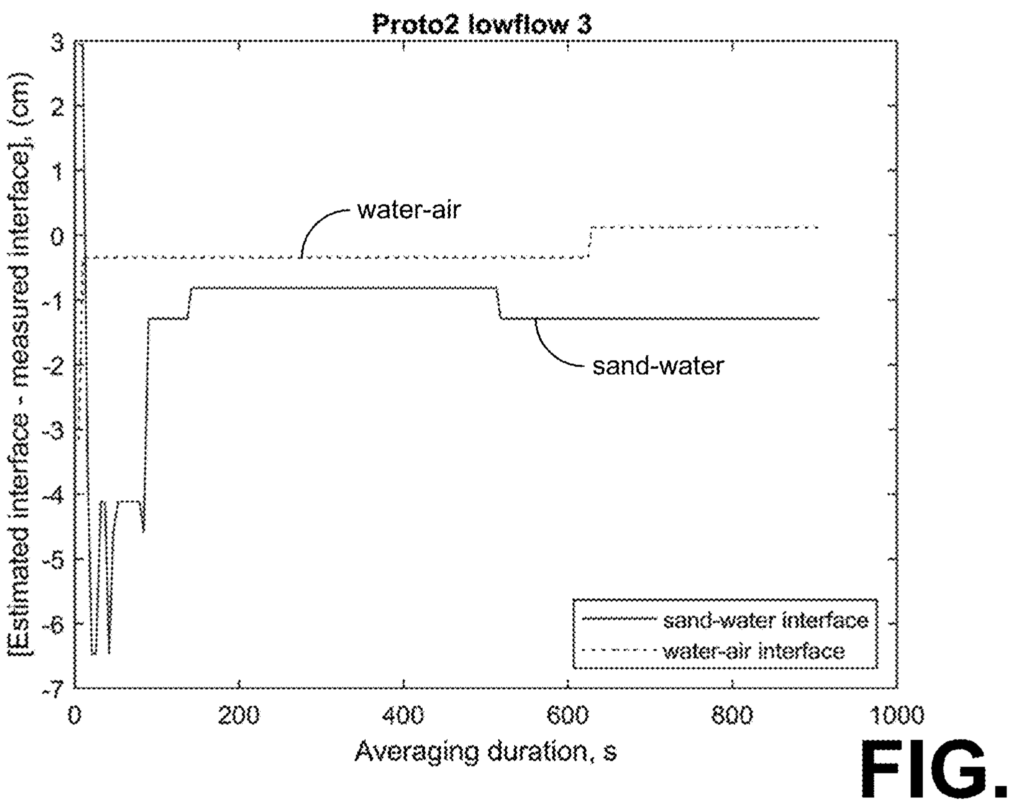

The results of the medium flow tests for three heat pulses can be seen in FIGS. 7A-7C. The x-axis is the mean temperature increase and the temperature gradient, and the y-axis is the height of the device in centimeters. The circle marker (704) represents the sand and water interface. The square marker (702) represents the water-air interface, and the difference between the two stars was the water depth. During these experiments, the velocity ranged from 2.36 cm/s to 3.15 cm/s. These results are similar to the no flow condition in regard to location of the interfaces. The sand-water interface was more clearly defined in FIGS. 7A-7C because of the greater temperature difference. FIGS. 7D-7F illustrate the associated error versus heating time increments for medium flow tests. The error in each test seemed to converge after 100 seconds of heating time.

Figure 8A:
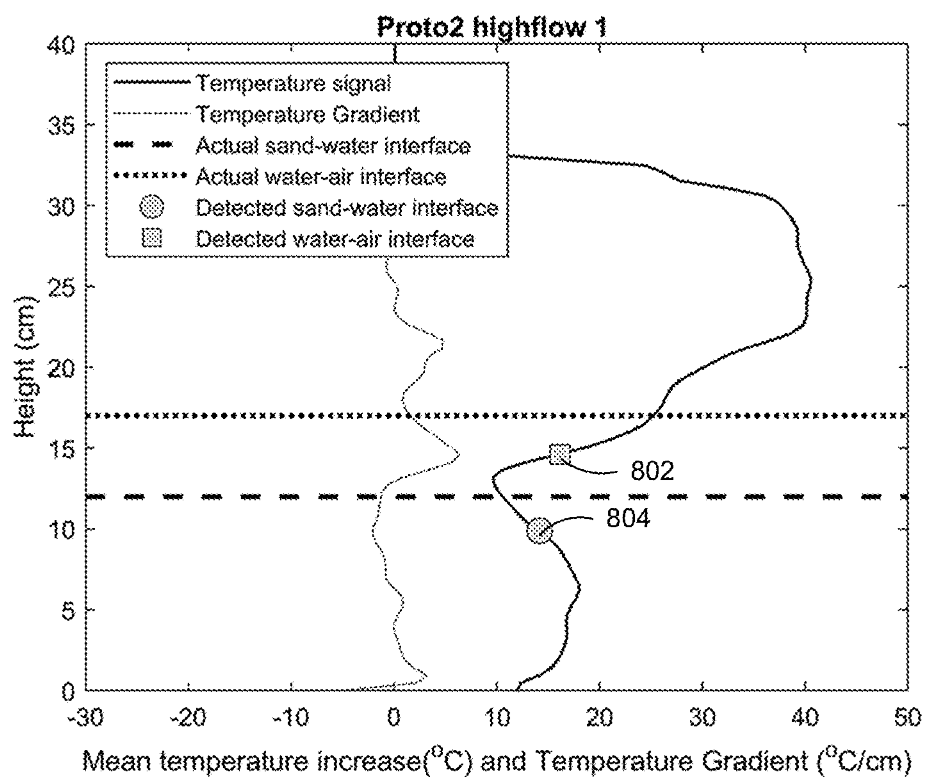
Figure 8B:
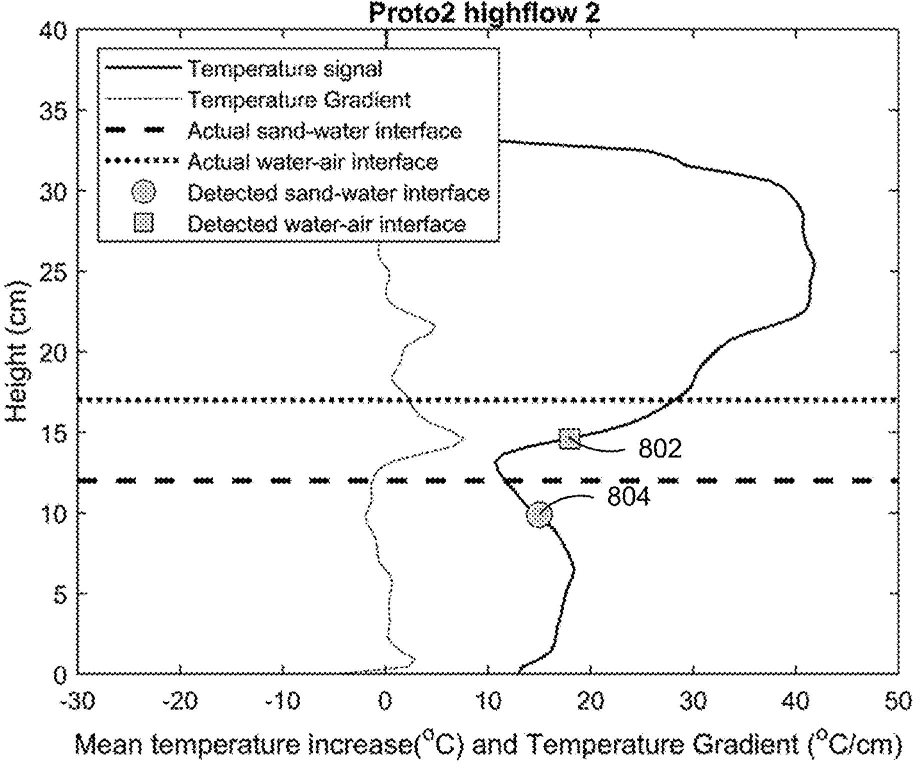
Figure 8C:
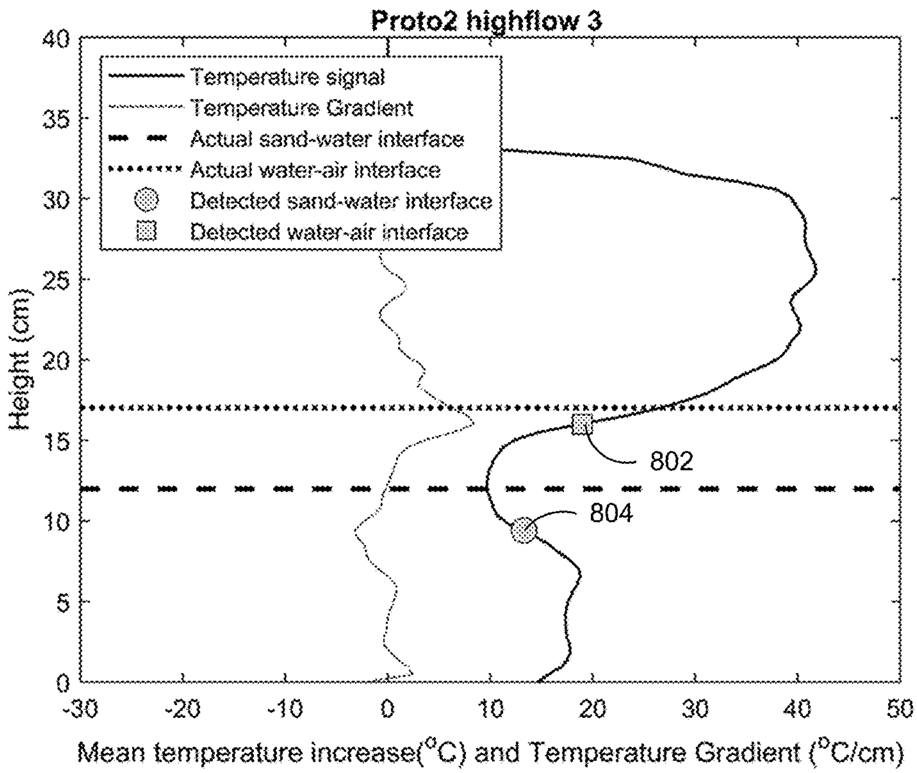
Figure 8D:
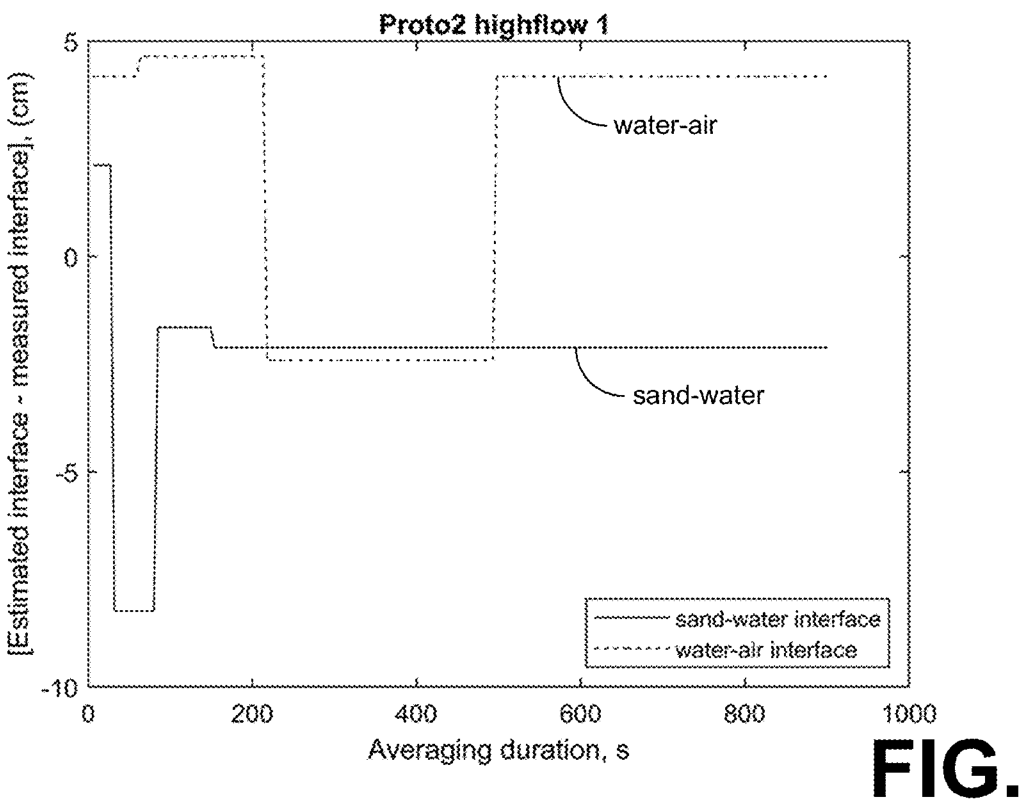
Figure 8E:
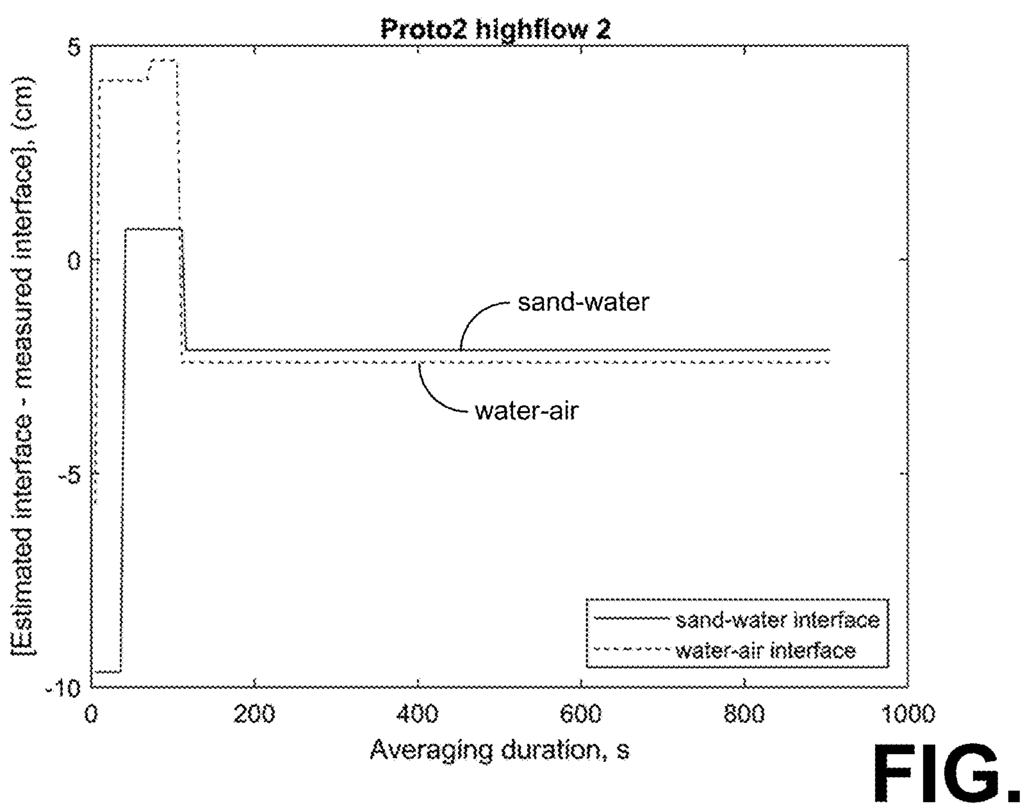
Figure 8F:
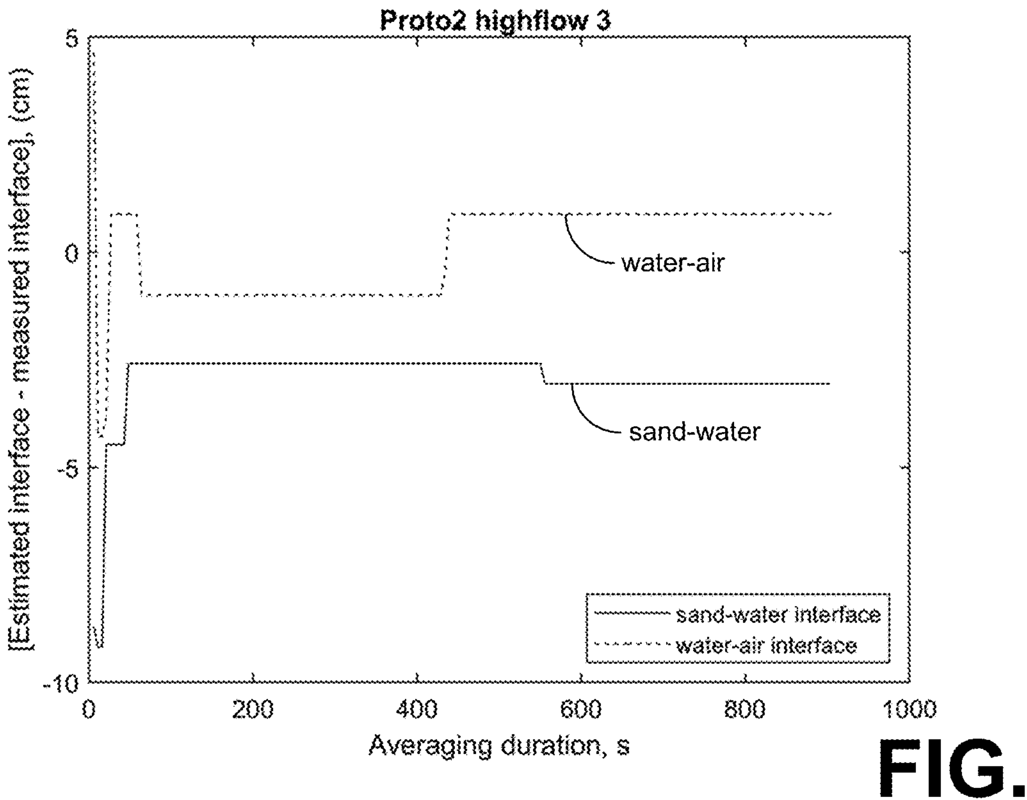

The results of the maximum flow test for three heat pulses can be seen in FIGS. 8A-8C. The x-axis is the mean temperature increase and the temperature gradient, and the y-axis is the height of the device in centimeters. The circle marker (804) represents the sand and water interface. The square marker (802) represents the water-air interface, and the difference between the two stars was the water depth. During these experiments, the velocity ranged from 8.85 cm/s to 15.92 cm/s. These results vary from the other conditions in that a slight scour hole did grow with respect to time and the water depth was much shallower. The maximum observed scour depth was approximately 1.5 cm according to the pictures taken during the experiments. The scour hole could have introduced errors to the reference measured locations of the interfaces that the device measurements were compared against. FIGS. 8D-8F illustrate the associated error versus heating time increments for maximum flow tests.

These tests most likely had the most variables changing between tests, resulting in greater differences between the observed and measured interfaces, e.g., the flow was producing scour around the sediment dynamics monitoring device during the test, and this scour formation could have been different in each test. Additionally, between each test the bed was smoothed, but it might have still had irregularities which could have impacted the measurements. The greater error occurred at the time intervals less than one minute. This indicates that a heating time of less than one minute is not adequate for capturing the sand-water interface.

The two major differences between Prototype 1 and Prototype 2 design are the density of vertical measurements and how heating was applied relatively to the location of the sensing cable. Those two major differences can explain the difference in performance observed between the two prototypes, i.e., the lower error value in detecting the water-sand interface location for prototype 1 and the faster response time in detecting the interface for prototype 2. In prototype 1, the combination of a higher resolution DTS unit and the use of a thinner FO cable, that can be more densely wrapped around the PVC core structure of the prototype, has resulted in higher vertical resolution of temperature measurements along the prototype, i.e., 0.126 cm for prototype 1 compared to the 1 cm resolution for prototype 2. On the other hand, the temperature sensing optical fiber in the FO cable of prototype 2 was in quasi direct contact and incased in the heating element. In contrast, the optical fiber in prototype 2 was separated by layers of thermally insulated material which created attenuation in the magnitude and lag in the arrival of the heating signal which resulted in a longer heating duration requirement to accurately locate the interfaces.

Field Installation Results

Preliminary results from the field tests performed at Ellerbe Creek have been analyzed. The time of active heating for each test was 5 minutes and the total amount of current was 10 amps, and the devices were connected in parallel.

Results were gathered from both sediment dynamics monitoring device 1 and sediment dynamics monitoring device 2. In FIG. 4, sediment dynamics monitoring device 1 was on the left side of the pier while sediment dynamics monitoring device 2 was directly on the downstream side of the pier. The water-air interface was not calculated because both sediment dynamics monitoring devices were entirely submerged in water.

Figure 9A:
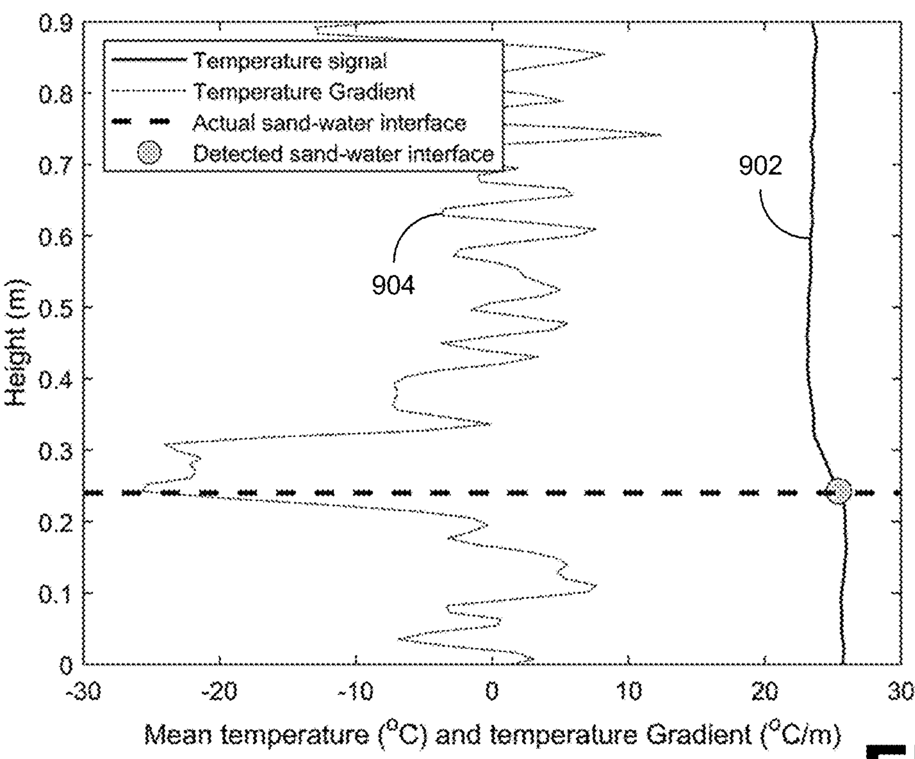
FIGS. 9A-9C and 10A-10B illustrate examples of in-field interface detection by the FO-DTS sediment dynamics monitoring device prototypes, in accordance with various embodiments of the present disclosure.
Figure 9B:
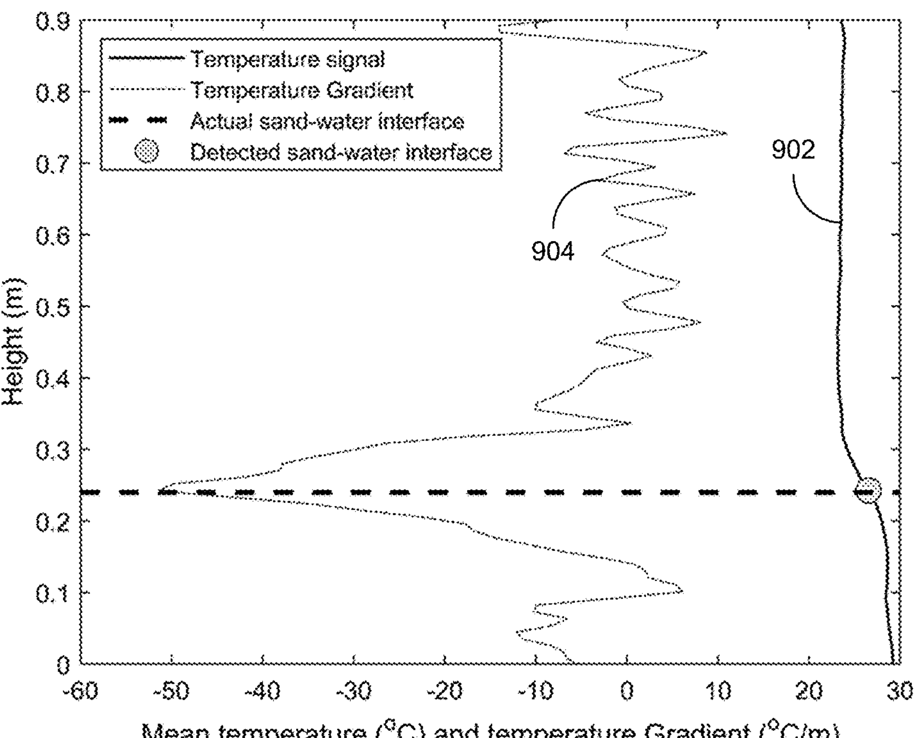
Figure 9C:
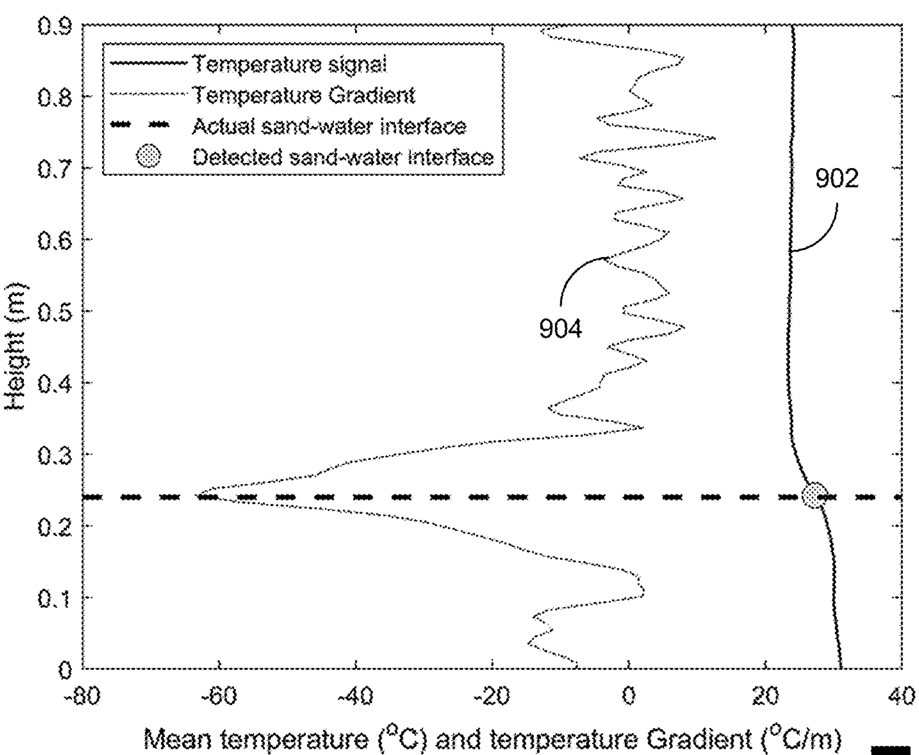

FIGS. 9A-9C shows the results of sediment dynamics monitoring device 1 for three heat pulses. Line 902 is the temperature signal, line 904 is the temperature gradient, the dashed line is the field-measured sand-water interface, and the circle marker is the algorithm-calculated sand-water interface. The error between these two values was around 1 cm, which is consistent with the laboratory experiments for prototype 2.

Figure 10A:
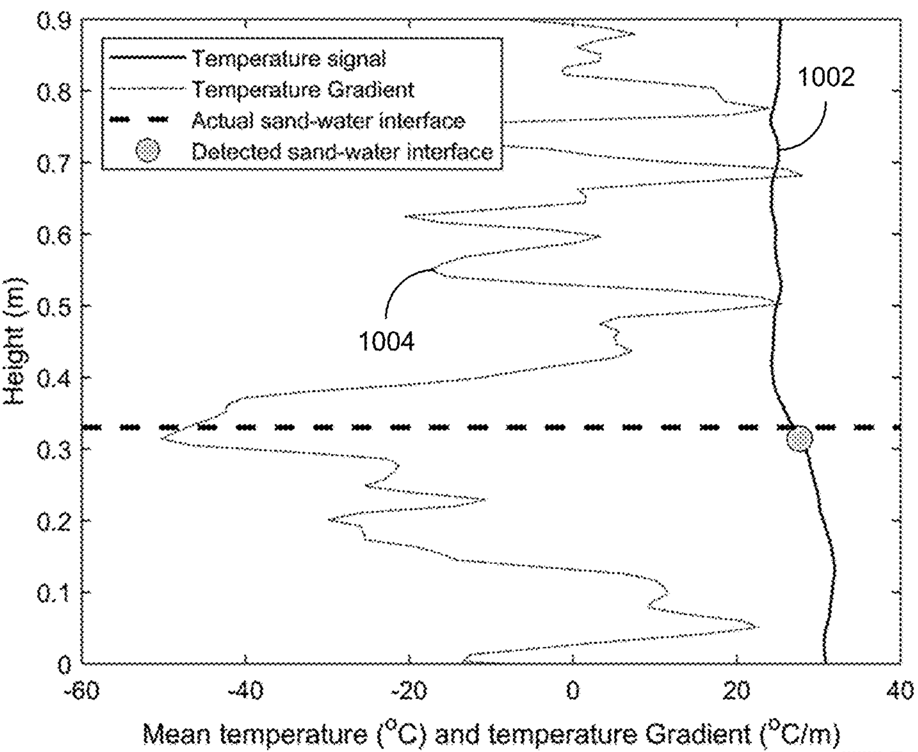
Figure 10B:
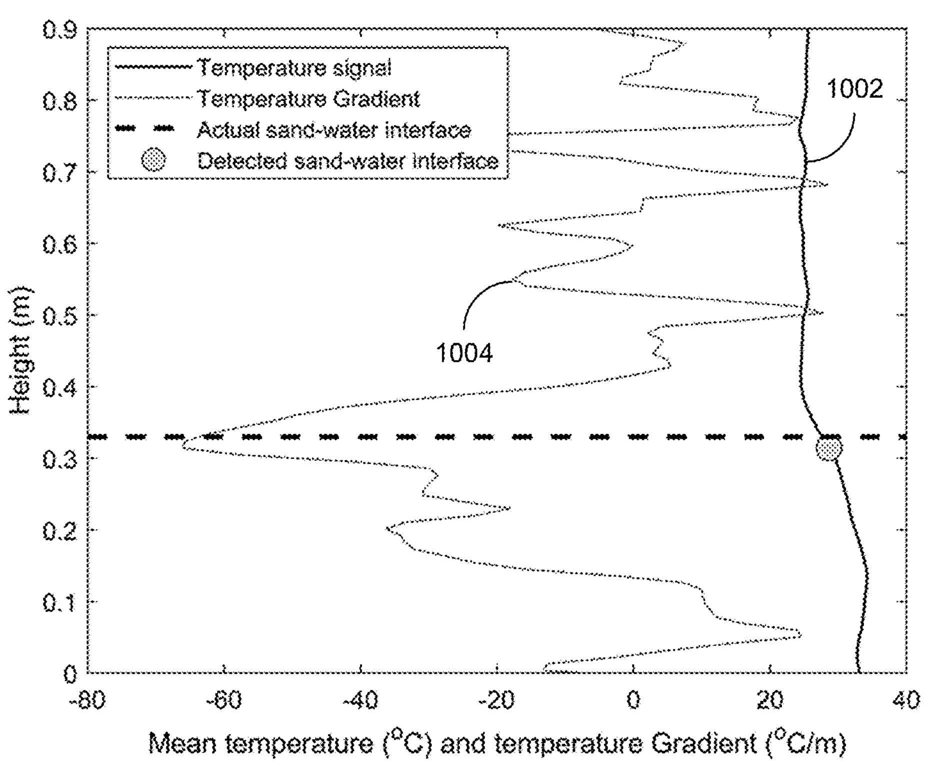

The results of sediment dynamics monitoring device 2 from the same time are shown in FIGS. 10A and 10B. Only two of the three heat pulses are shown below due to an incomplete dataset for the first test on sediment dynamics monitoring device 2, which meant that it was not possible to solve for the selected interfaces. However, between the remaining two tests the results are consistent. The error was 1 cm for these tests, which again is consistent with the laboratory experiments of prototype 2.

In this disclosure, two prototype FO-DTS sediment dynamics monitoring devices were tested in the lab and eventually one of those was tested in the field. The advantage of prototype 1 when compared to prototype 2 was that it had increased vertical resolution in detecting the water-sediment interface. The construction of the prototype 1 was more laboring than prototype 2 because the heating cable was wrapped on top of the FO cable allowing more chance of the FO-cable being distorted. Additionally, because the heating cable was wrapped above the FO-cable, the time to detect the applied heating was longer. For this reason, more frequent measurements can be achieved with prototype 2 than prototype 1, which can be beneficial to accurately characterize a rapidly changing interface location in dynamic scouring. Furthermore, a practical advantage of prototype 2 was the robustness of the FO cable used when compared to the more fragile cable used in prototype 1. Such an advantage can be important to long-term deployment in river systems with flow charged with debris that can damage the prototype.

The error in detecting the sand-water interface for prototype 1 converged around zero, however, for prototype 2 this error most often converged around 1 cm. This error magnitude for both prototypes reflects the combination of vertical resolutions of each of the prototypes and the DTS unit resolution used in the experiment. Because only one laboratory experiment of each condition was performed for prototype 1, the consistency within the tests cannot be determined, but for prototype 2 the laboratory results were consistent within each testing condition. The most range in error occurred during the high flow test. This could have been a result of the scour that was taking place around the sediment dynamics monitoring device.

By analyzing the error over heating time duration for both prototypes, the ideal heating time was determined. Around 100 seconds in each test of prototype 2 and 300 seconds for prototype 1, the sand-water interface error stabilized or was the minimum. This means that when prototype 2 is deployed a 100 second heat pulse could be applied instead of a 300 second heat pulse, and this would save time to run more experiments in one sitting.

Therefore, it was decided that the field sediment dynamics monitoring device should be constructed using the same materials as that of prototype 2. The FO cable used for the field device had to be very durable against floating debris and animals. The device was tested in the field with promising results so far. The error was 1 to 2 cm which was similar to the error in the laboratory tests.

Each of the experiments proved that the sand-water interface and air-water interface could be discerned using the developed algorithm. The test results provide a proof of concept for the FO-DTS sediment dynamics monitoring devices detecting scour under ranges of flow, with different device construction, under laboratory and field conditions. FO-DTS offers a better way to measure bridge pier scour because of its superior durability and proven accuracy.

Figure 11:
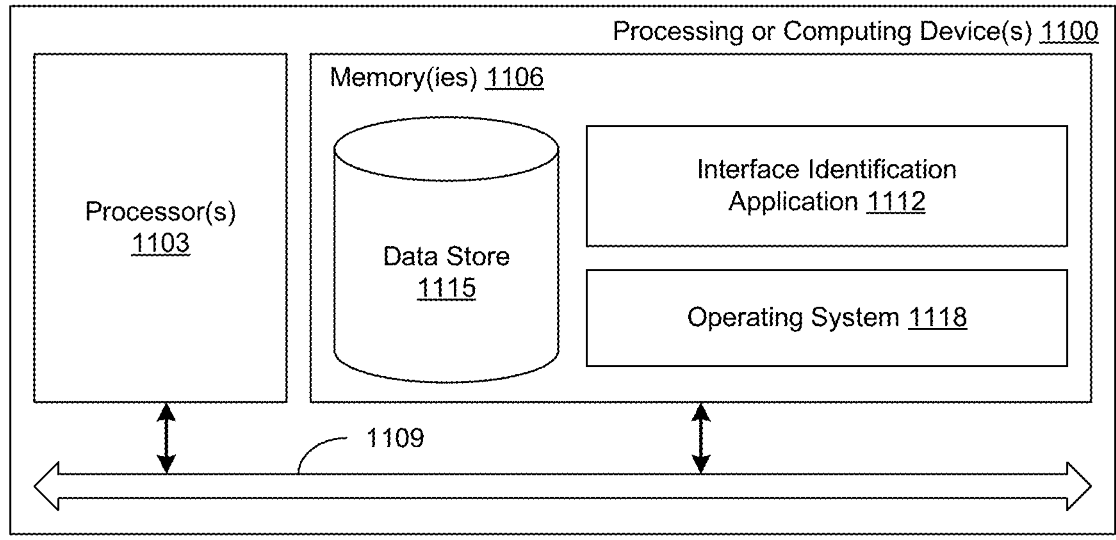
FIG. 11 is a schematic block diagram illustrating an example of a processing or computing device, in accordance with various embodiments of the present disclosure.

Referring to FIG. 11, shown is an example of a processing or computing device 1100 that may be utilized for the methodology disclosed herein. The processing or computing device 1100 can be the DTS 115 or the processing or computing device 1100 can be a device in communication with a sensing device as part of the DTS system 115. The processing or computing device 1100 can be one or more processing or computing device(s), which includes at least one processor circuit, for example, having a processor 1103 and a memory 1106, both of which are coupled to a local interface 1109. To this end, the processing or computing device 1100 may comprise, for example, a server computer, mobile computing device (e.g., laptop, tablet, smart phone, etc.) or any other system providing computing capability. The processing or computing device 1100 may include, for example, one or more display or touch screen devices and various peripheral devices. The local interface 1109 may comprise, for example, a data bus with an accompanying address/control bus or other bus structure as can be appreciated.

Stored in the memory 1106 are both data and several components that are executable by the processor 1103. In particular, stored in the memory 1106 and executable by the processor 1103 include a interface identification application 1112 and potentially other applications. Also stored in the memory 1106 may be a data store 1115 and other data. The data stored in the data store 1115, for example, is associated with the operation of the various applications and/or functional entities as described. For example, the data store may include databases, engines, models, object libraries, and other data or information as can be understood. In addition, an operating system 1118 may be stored in the memory 1106 and executable by the processor 1103. The data store 1106 may be located in a processing or computing device 1100 or may be dispersed among many different devices. The components executed on the processing or computing device 1100 include, for example, the interface identification application 1112 and other systems, applications, services, processes, engines, or functionality not discussed in detail herein. It is understood that there may be other applications that are stored in the memory 1106 and are executable by the processor 1103 as can be appreciated. Where any component discussed herein is implemented in the form of software, any one of a number of programming languages may be employed.

The processing or computing device 1100 can be the DTS 115 or can be configured to communicate with one or more DTS 115. For example, the DTS 115 can be communicatively coupled to the processing or computing device 1100 either directly through a wireless communication link or other appropriate wired or wireless communication channel, or indirectly through an IP network (e.g., WLAN, internet, cellular or other appropriate network or combination of networks). In this way, information acquired by the DTS 115 can be communicated to the processing or computing device 1100 for analysis and processing.

A number of software components are stored in the memory 1106 and are executable by the processor 1103. In this respect, the term "executable" means a program file that is in a form that can ultimately be run by the processor 1103. Examples of executable programs may be, for example, a compiled program that can be translated into machine instructions in a format that can be loaded into a random access portion of the memory 1106 and run by the processor 1103, source code that may be expressed in proper format such as object code that is capable of being loaded into a random access portion of the memory 1106 and executed by the processor 1103, or source code that may be interpreted by another executable program to generate instructions in a random access portion of the memory 1106 to be executed by the processor 1103, etc. An executable program may be stored in any portion or component of the memory 1106 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

Also, the processor 1103 may represent multiple processors 1103 and the memory 1106 may represent multiple memories 1106 that operate in parallel processing circuits, respectively. In such a case, the local interface 1109 may be an appropriate network that facilitates communication between any two of the multiple processors 1103, between any processor 1103 and any of the memories 1106, or between any two of the memories 1106, etc. The local interface 1109 may comprise additional systems designed to coordinate this communication, including, for example, performing load balancing. The processor 1103 may be of electrical or of some other available construction.

Although the interface identification application 1112, and other various systems described herein, may be embodied in software or instructions executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Figure 12:
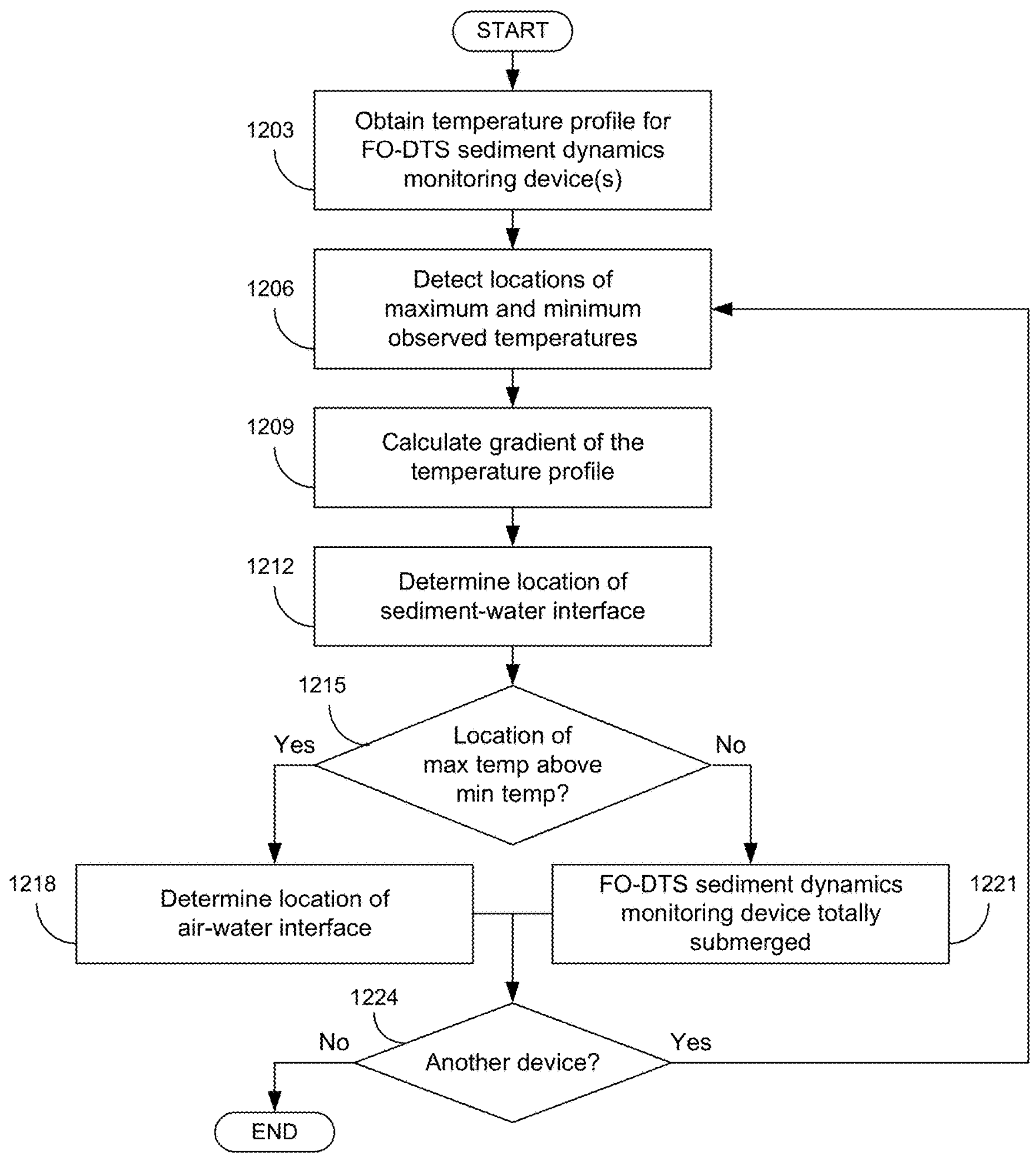
FIG. 12 is a flow chart illustrating an example of an interface identification process, in accordance with various embodiments of the present disclosure.

Any logic or application described herein, including the interface identification application 1112, that comprises software or instructions can be embodied in any non-transitory computer-readable medium for use by or in connection with an instruction execution system such as, for example, a processor 1106 in a processing or computing device 1100 or other system. In this sense, the logic may comprise, for example, statements including instructions and declarations that can be fetched from the computer-readable medium and executed by the instruction execution system. The flowcharts or diagrams of FIG. 12 show examples of the architecture, functionality, and operation of possible implementations of a interface identification application 1112. In this regard, each block can represent a module, segment, or portion of code, which comprises one or more executable instructions for implementing the specified logical function(s). It should also be noted that in some alternative implementations, the functions noted in the blocks may occur out of the order noted in FIG. 12. For example, two blocks shown in succession in FIG. 12 may in fact be executed substantially concurrently or the blocks may sometimes be executed in a different or reverse order, depending upon the functionality involved. Alternate implementations are included within the scope of the preferred embodiment of the present disclosure in which functions may be executed out of order from that shown or discussed, including substantially concurrently or in reverse order, depending on the functionality involved, as would be understood by those reasonably skilled in the art of the present disclosure.

Communication media appropriate for use in or with the inventions of the present disclosure may be exemplified by computer-readable instructions, data structures, program modules, or other data stored on non-transient computer-readable media, and may include any information-delivery media. The instructions and data structures stored on the non-transient computer-readable media may be transmitted as a modulated data signal to the computer or server on which the computer-implemented methods of the present disclosure are executed. A “modulated data signal” may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term “computer-readable media” as used herein may include both local non-transient storage media and remote non-transient storage media connected to the information processors using communication media such as the internet. Non-transient computer-readable media do not include mere signals or modulated carrier waves, but include the storage media that form the source for such signals.

In the context of the present disclosure, a “computer-readable medium” can be any medium that can contain, store, or maintain the logic or application described herein for use by or in connection with the instruction execution system. The computer-readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

In the context of the present disclosure, a “computer-readable medium” can be any medium that can contain, store, or maintain the logic or application described herein for use by or in connection with the instruction execution system. The computer-readable medium can comprise any one of many physical media such as, for example, electronic, magnetic, optical, electromagnetic, infrared, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Referring next to FIG. 12, shown is a flow chart illustrating an example of an interface identification process, in accordance with various embodiments of the present disclosure. Beginning at 1203, a temperature profile is obtained for one or more FO-DTS sediment dynamics monitoring device(s). Distributed temperature sensing can be used to measure the temperature profile along a fiber optic cable wound around a support structure of the FO-DTS sediment dynamics monitoring device, which can be positioned within a waterway or other fluid path. At 1206, the locations of the maximum observed temperature and the minimum observed temperature are determined along the FO-DTS sediment dynamics monitoring device. These can be detected using the measured temperature profile. A gradient of the measured temperature profile can also be calculated at 1209.

The location of the sediment-water interface can be determined at 1212 based upon the gradient of the temperature profile. The location of the sediment-water interface corresponds to a location of a minimum temperature gradient observed between an end of the FO-DTS sediment dynamics monitoring device located inside the sediment and the location of the minimum observed temperature. At 1215, the presence of an air-water interface along the FO-DTS sediment dynamics monitoring device is determined can be determined. If the location of the maximum observed temperature is above the location of the minimum observed temperature (i.e., not between an end of the FO-DTS sediment dynamics monitoring device located inside the sediment and the location of the minimum observed temperature), then the location of the air-water interface is determined at 1218. The location of the air-water interface corresponds to a location of a maximum temperature gradient observed between the location of the minimum observed temperature and the location of the maximum observed temperature. However, if the location of the maximum observed temperature is not above the location of the minimum observed temperature at 1215, then the FO-DTS sediment dynamics monitoring device is totally submerged at 1221. If multiple FO-DTS sediment dynamics monitoring devices are being monitored, it can be determined if another device should be evaluated at 1224. If yes, then the process flow can return to 1206 to determine the minimum and maximum temperature locations for the next FO-DTS sediment dynamics monitoring device. Otherwise the process can end. The process can be repeated to determine changes in the interface locations or interface locations of other FO-DTS sediment dynamics monitoring devices.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A sediment dynamics monitoring system for scour, erosion or deposition detection, comprising:
- a fiber-optic distributed temperature sensing (FO-DTS) sediment dynamics monitoring device comprising:
  - a support structure;
  - a FO cable wound around the support structure, the FO cable providing continuous sensing along a length of the support structure; and
  - a heating element collocated along the FO cable, wherein the heating element is wrapped on the FO cable opposite the support structure;
- a power controller configured to control heating of the heating element; and
- a distributed temperature sensing (DTS) system configured to measure a temperature profile along a length of the FO cable, wherein an anomaly in the measured temperature profile indicates an interface surrounding the FO-DTS sediment dynamics monitoring device.

2. A sediment dynamics monitoring system for scour, erosion or deposition detection, comprising:
- a fiber-optic distributed temperature sensing (FO-DTS) sediment dynamics monitoring device comprising:
  - a support structure;
  - a FO cable wound around the support structure, the FO cable providing continuous sensing along a length of the support structure; and
  - a heating element collocated along the FO cable;
- a power controller configured to control heating of the heating element; and
- a distributed temperature sensing (DTS) system configured to measure a temperature profile along a length of the FO cable, wherein an anomaly in the measured temperature profile indicates an interface surrounding the FO-DTS sediment dynamics monitoring device;
- wherein the FO-DTS sediment dynamics monitoring device is positioned in sediment of a waterway and the interface is a sediment-water interface or an air-water interface and the DTS system is configured to:
- detect a location of a minimum observed temperature along the FO-DTS sediment dynamics monitoring device;
- calculate a gradient of the measured temperature profile; and
- determine a location of the sediment-water interface, wherein the location of the sediment-water interface corresponds to a location of a minimum temperature gradient observed between an end of the FO-DTS sediment dynamics monitoring device located inside the sediment and the location of the minimum observed temperature.

3. The sediment dynamics monitoring system of claim 1, wherein the temperature profile corresponds to a heat pulse applied to the heating element for a defined period of time.

4. The sediment dynamics monitoring system of claim 3, wherein the power controller controls application of power to the heating element over the defined period of time.

5. The sediment dynamics monitoring system of claim 2, wherein the heating element is incorporated in the FO cable or is wrapped adjacent to the FO cable.

6. The sediment dynamics monitoring system of claim 5, wherein the heating element comprises wires distributed about one or more optical fiber of the FO cable.

7. The sediment dynamics monitoring system of claim 1, wherein the FO-DTS sediment dynamics monitoring device is positioned in sediment of a waterway and the interface is a sediment-water interface or an air-water interface.

8. The sediment dynamics monitoring system of claim 2, wherein the DTS system is further configured to:

detect a location of a maximum observed temperature along the FO-DTS sediment dynamics monitoring device; and determine a location of an air-water interface in response to the location of the maximum observed temperature being above the location of the minimum observed temperature, wherein the location of the air-water interface corresponds to a location of a maximum temperature gradient observed between the location of the minimum observed temperature and the location of the maximum observed temperature.

9. The sediment dynamics monitoring system of claim 8, wherein the FO-DTS sediment dynamics monitoring device is totally submerged underwater if the location of the maximum observed temperature is below the location of the minimum observed temperature.

10. The sediment dynamics monitoring system of claim 2, wherein the DTS system is configured to identify a location of the interface along the length of the support structure based upon the temperature profile.

11. The sediment dynamics monitoring system of claim 10, wherein the interface is identified based upon a temperature gradient of the temperature profile.

12. The sediment dynamics monitoring system of claim 11, wherein the DTS system is configured to:

detect locations of a maximum observed temperature and a minimum observed temperature of an observed temperature profile along the FO-DTS sediment dynamics monitoring device;

calculate the temperature gradient of the observed temperature profile;

determine a location of a sediment-water interface, wherein the location of the sediment-water interface corresponds to a location of a minimum temperature gradient observed between a lower end of the FO-DTS sediment dynamics monitoring device and the location of the minimum observed temperature; and determine a location of an air-water interface if the location of the maximum observed temperature being above the location of the minimum observed temperature, wherein the location of the air-water interface corresponds to a location of a maximum temperature gradient observed between the location of the minimum observed temperature and the location of the maximum observed temperature.

13. A sediment dynamics monitoring system for scour, erosion or deposition detection, comprising:

a fiber-optic distributed temperature sensing (FO-DTS) sediment dynamics monitoring device comprising:

a support structure;

a FO cable wound around the support structure, the FO cable providing continuous sensing along a length of the support structure; and a heating element collocated along the FO cable;

a power controller configured to control heating of the heating element; and a distributed temperature sensing (DTS) system configured to measure a temperature profile along a length of the FO cable, wherein an anomaly in the measured temperature profile indicates an interface surrounding the FO-DTS sediment dynamics monitoring device, wherein the DTS system is configured to identify a location of the interface along the length of the support structure based upon the temperature profile and the identified location of the interface is a water-air interface.

14. The sediment dynamics monitoring system of claim 13, wherein the DTS system is configured to determine water velocity about the FO-DTS sediment dynamics monitoring device based at least in part upon the temperature profile.

15. The sediment dynamics monitoring system of claim 13, wherein the DTS system is configured to identify a location of a second interface along the length of the support structure based upon the temperature profile.

16. The sediment dynamics monitoring system of claim 15, wherein the identified locations of the interfaces comprise the sediment-water interface and the water-air interface.

17. The sediment dynamics monitoring system of claim 16, wherein the DTS system is configured to determine air velocity about the FO-DTS sediment dynamics monitoring device based at least in part upon the temperature profile.

18. The sediment dynamics monitoring of system of claim 17, wherein the DTS system is configured to determine rate and amount of sediment movement about the FO-DTS sediment dynamics monitoring device based at least in part upon the temperature profile within the portion of the FO-DTS sediment dynamics monitoring device buried within the sediment.

19. The sediment dynamics monitoring system of claim 2, wherein the temperature profile corresponds to a heat pulse applied to the heating element for a defined period of time.

20. The sediment dynamics monitoring system of claim 13, wherein the temperature profile corresponds to a heat pulse applied to the heating element for a defined period of time.

* * * * *